United States Patent
Robinson et al.

(10) Patent No.: US 10,074,199 B2
(45) Date of Patent: Sep. 11, 2018

(54) SYSTEMS AND METHODS FOR TISSUE MAPPING

(71) Applicant: TRACTUS CORPORATION, Austin, TX (US)

(72) Inventors: Bruce Alexander Robinson, Maple Valley, WA (US); Scott Powers Huntley, Danville, CA (US); Janice Marie Whyte, Sebastapol, CA (US)

(73) Assignee: TRACTUS CORPORATION, Austin, TX (US)

( * ) Notice: Subject to any disclaimer, the term of this patent is extended or adjusted under 35 U.S.C. 154(b) by 48 days.

(21) Appl. No.: 14/900,460

(22) PCT Filed: Jun. 27, 2014

(86) PCT No.: PCT/US2014/044522
§ 371 (c)(1),
(2) Date: Dec. 21, 2015

(87) PCT Pub. No.: WO2014/210430
PCT Pub. Date: Dec. 31, 2014

(65) Prior Publication Data
US 2016/0155247 A1    Jun. 2, 2016

Related U.S. Application Data

(60) Provisional application No. 61/840,277, filed on Jun. 27, 2013.

(51) Int. Cl.
*G06K 9/00*        (2006.01)
*G06T 11/00*       (2006.01)
(Continued)

(52) U.S. Cl.
CPC .......... *G06T 11/006* (2013.01); *A61B 8/0825* (2013.01); *A61B 8/4254* (2013.01);
(Continued)

(58) Field of Classification Search
None
See application file for complete search history.

(56) References Cited

U.S. PATENT DOCUMENTS 4,094,306 A    6/1978  Kossoff
4,121,468 A   10/1978  Glover et al.
(Continued)

FOREIGN PATENT DOCUMENTS

CN     1305443 C     3/2007
CN   101657736 A     2/2010
(Continued)

OTHER PUBLICATIONS

American College of Radiology; ACR Practice Guideline for the Performance of Screening and Diagnostic Mammography; pp. 1-10; Res. 24; Oct. 2008.
(Continued)

*Primary Examiner* — Nancy Bitar
(74) *Attorney, Agent, or Firm* — Shay Glenn LLP

(57) ABSTRACT

Tissue mapping and imaging systems are disclosed along with methods for mapping tissue. The systems can include an image recording and mapping system in communication with a manual image scanning device having an imaging probe. The manual image scanning device can be configured to scan a volume of tissue and output at least one scanned image and to electronically receive and record the at least one scanned image. The image recording and mapping system can be further configured to construct an idealized tissue map from the at least one scanned image. The image recording and mapping system can also include a position tracking system configured to detect and track the position of the imaging probe and provide location identifier information for the at least one scanned image. The idealized
(Continued)

tissue map can be an idealized depiction of an anatomy. The idealized tissue map can include references points.

10 Claims, 38 Drawing Sheets

(51) Int. Cl.
*A61B 8/08* (2006.01)
*A61B 8/00* (2006.01)
*G06T 7/00* (2017.01)
*G06T 7/73* (2017.01)

(52) U.S. Cl.
CPC .......... *A61B 8/4416* (2013.01); *G06T 7/0012* (2013.01); *G06T 7/74* (2017.01); *G06T 11/005* (2013.01); *G06T 11/008* (2013.01); *G06T 2207/30068* (2013.01)

(56) References Cited

U.S. PATENT DOCUMENTS

| | | | |
|---|---|---|---|
| 4,228,804 A | 10/1980 | Holasek et al. | |
| 4,347,850 A | 9/1982 | Kelly et al. | |
| 4,397,531 A | 8/1983 | Lees | |
| 4,478,083 A | 10/1984 | Hassler et al. | |
| 4,478,084 A | 10/1984 | Hassler et al. | |
| 4,486,080 A | 12/1984 | Itoh et al. | |
| 4,489,729 A | 12/1984 | Sorenson et al. | |
| 4,905,700 A | 3/1990 | Wokalek et al. | |
| 4,938,067 A | 7/1990 | Karaki et al. | |
| 4,953,111 A | 8/1990 | Yamamoto et al. | |
| 5,152,290 A | 10/1992 | Freeland | |
| 5,318,028 A | 6/1994 | Mitchell et al. | |
| 5,329,929 A | 7/1994 | Sato et al. | |
| 5,333,612 A | 8/1994 | Wild | |
| 5,353,354 A | 10/1994 | Keller et al. | |
| 5,398,691 A | 3/1995 | Martin et al. | |
| 5,410,376 A | 4/1995 | Cornsweet et al. | |
| 5,424,636 A | 6/1995 | Rollwage et al. | |
| 5,454,371 A | 10/1995 | Fenster et al. | |
| 5,455,601 A | 10/1995 | Ozaki | |
| 5,562,095 A | 10/1996 | Downey et al. | |
| 5,570,698 A | 11/1996 | Liang et al. | |
| 5,588,434 A | 12/1996 | Fujimoto | |
| 5,638,084 A * | 6/1997 | Kalt .................. G09F 9/372 345/31 |
| 5,640,956 A | 6/1997 | Getzinger et al. | |
| 5,664,573 A | 9/1997 | Shmulewitz | |
| 5,786,765 A | 7/1998 | Kumakura et al. | |
| 5,787,889 A | 8/1998 | Edwards et al. | |
| 5,833,634 A | 11/1998 | Laird et al. | |
| 5,842,473 A | 12/1998 | Fenster et al. | |
| 5,860,934 A | 1/1999 | Sarvazyan | |
| 5,867,587 A | 2/1999 | Aboutalib et al. | |
| 5,873,830 A | 2/1999 | Hossack et al. | |
| 5,905,563 A | 5/1999 | Yamamoto | |
| 5,964,707 A | 10/1999 | Fenster et al. | |
| 5,984,870 A | 11/1999 | Giger et al. | |
| 5,989,199 A | 11/1999 | Cundari et al. | |
| 6,002,958 A | 12/1999 | Godik | |
| 6,012,458 A | 1/2000 | Mo et al. | |
| 6,067,075 A | 5/2000 | Pelanek | |
| 6,091,334 A | 7/2000 | Galiana et al. | |
| 6,117,080 A | 9/2000 | Schwartz | |
| 6,119,033 A | 9/2000 | Spigelman et al. | |
| 6,128,523 A | 10/2000 | Bechtold et al. | |
| 6,201,900 B1 | 3/2001 | Hossack et al. | |
| 6,228,028 B1 | 5/2001 | Klein et al. | |
| 6,248,071 B1 | 6/2001 | Lin | |
| 6,280,387 B1 | 8/2001 | DeForge et al. | |
| 6,351,273 B1 | 2/2002 | Lemelson et al. | |
| 6,461,298 B1 | 10/2002 | Fenster et al. | |
| 6,517,491 B1 | 2/2003 | Thiele et al. | |
| 6,520,915 B1 | 2/2003 | Lin et al. | |
| 6,524,246 B1 | 2/2003 | Kelly et al. | |
| 6,524,247 B2 | 2/2003 | Zhao et al. | |
| 6,524,252 B1 | 2/2003 | Yu et al. | |
| 6,540,681 B1 | 4/2003 | Cheng et al. | |
| 6,547,730 B1 | 4/2003 | Lin et al. | |
| 6,603,491 B2 | 8/2003 | Lemelson et al. | |
| 6,675,038 B2 | 1/2004 | Cupples et al. | |
| 6,695,786 B2 | 2/2004 | Wang et al. | |
| 6,701,341 B1 | 3/2004 | Wu et al. | |
| 6,825,838 B2 | 11/2004 | Smith et al. | |
| 6,839,762 B1 | 1/2005 | Yu et al. | |
| 6,970,587 B1 * | 11/2005 | Rogers .................. G06T 7/0012 128/922 |
| 6,988,991 B2 | 1/2006 | Kim et al. | |
| 7,018,333 B2 | 3/2006 | Wang et al. | |
| 7,103,205 B2 | 9/2006 | Wang et al. | |
| 7,253,738 B2 | 8/2007 | Hammoud et al. | |
| 7,253,739 B2 | 8/2007 | Hammoud et al. | |
| 7,556,602 B2 | 7/2009 | Wang et al. | |
| 7,597,663 B2 | 10/2009 | Wang et al. | |
| 7,610,250 B2 | 10/2009 | Kisacanin et al. | |
| 7,615,008 B2 | 11/2009 | Zhang et al. | |
| 7,639,146 B2 | 12/2009 | Baura | |
| 7,659,923 B1 | 2/2010 | Johnson | |
| 7,676,063 B2 | 3/2010 | Cohen et al. | |
| 7,714,927 B2 | 5/2010 | Terashima | |
| 7,722,565 B2 | 5/2010 | Wood et al. | |
| 7,727,151 B2 | 6/2010 | Zhang et al. | |
| 7,731,662 B2 | 6/2010 | Anderson et al. | |
| 7,746,235 B2 | 6/2010 | Hammoud et al. | |
| 7,751,868 B2 | 7/2010 | Glossop | |
| 7,783,347 B2 | 8/2010 | Abourizk et al. | |
| 7,805,269 B2 | 9/2010 | Glossop | |
| 7,830,266 B2 | 11/2010 | Nakagoshi et al. | |
| 7,918,807 B2 | 4/2011 | Lau et al. | |
| 7,940,966 B2 | 5/2011 | Yu et al. | |
| 7,940,970 B2 | 5/2011 | Levanon et al. | |
| 8,077,215 B2 | 12/2011 | Nakamura | |
| 8,096,949 B2 | 1/2012 | Chen et al. | |
| 8,102,417 B2 | 1/2012 | Hammoud et al. | |
| 8,157,734 B2 | 4/2012 | Nakata | |
| 8,203,599 B2 | 6/2012 | Kim et al. | |
| 8,314,707 B2 | 11/2012 | Kobetski et al. | |
| 9,256,283 B2 * | 2/2016 | Kang .................. G06F 3/011 |
| 9,597,008 B2 * | 3/2017 | Henkel .................. A61B 8/0833 |
| 2003/0176791 A1 | 9/2003 | Rabiner et al. | |
| 2003/0204139 A1 | 10/2003 | Hashimoto | |
| 2004/0077943 A1 | 4/2004 | Meaney et al. | |
| 2004/0167402 A1 | 8/2004 | Jones et al. | |
| 2004/0206913 A1 | 10/2004 | Costa et al. | |
| 2004/0241832 A1 | 12/2004 | Muraki et al. | |
| 2005/0096539 A1 | 5/2005 | Leibig et al. | |
| 2005/0110881 A1 | 5/2005 | Giukhovsky et al. | |
| 2006/0050993 A1 | 3/2006 | Stentiford | |
| 2006/0241430 A1 | 10/2006 | Lin | |
| 2006/0280348 A1 | 12/2006 | Smith et al. | |
| 2007/0071354 A1 | 3/2007 | Florent et al. | |
| 2007/0255137 A1 | 11/2007 | Sui et al. | |
| 2007/0273926 A1 | 11/2007 | Sugiyama et al. | |
| 2008/0021317 A1 | 1/2008 | Sumanweera | |
| 2008/0056548 A1 | 3/2008 | Irarrazaval et al. | |
| 2008/0208041 A1 | 8/2008 | Gilboa | |
| 2009/0018441 A1 | 1/2009 | Willsie et al. | |
| 2009/0041323 A1 | 2/2009 | LaChaine et al. | |
| 2009/0087046 A1 | 4/2009 | Kuhn | |
| 2009/0105582 A1 | 4/2009 | Dougherty et al. | |
| 2010/0046797 A1 | 2/2010 | Strat et al. | |
| 2010/0079508 A1 | 4/2010 | Hodge et al. | |
| 2010/0130863 A1 | 5/2010 | Kelly | |
| 2010/0168580 A1 | 7/2010 | Thiele | |
| 2010/0226555 A1 | 9/2010 | Sandstrom et al. | |
| 2010/0298705 A1 | 11/2010 | Pelissier et al. | |
| 2010/0328492 A1 | 12/2010 | Fedorovskaya et al. | |
| 2011/0066174 A1 | 3/2011 | Gilbert | |
| 2011/0079082 A1 | 4/2011 | Yoo et al. | |
| 2011/0201914 A1 | 8/2011 | Wang et al. | |
| 2011/0224550 A1 | 9/2011 | Shinohara | |
| 2012/0183188 A1 | 7/2012 | Moriya | |
| 2012/0302289 A1 | 11/2012 | Kang | |

(56) References Cited

U.S. PATENT DOCUMENTS

| | | |
|---|---|---|
| 2012/0302884 A1 | 11/2012 | Sandstrom et al. |
| 2012/0316441 A1 | 12/2012 | Toma et al. |
| 2013/0023767 A1 | 1/2013 | Mammone |
| 2013/0127909 A1 | 5/2013 | Nichols et al. |
| 2013/0225986 A1* | 8/2013 | Eggers .............. A61B 8/0825 600/425 |
| 2015/0213725 A1 | 7/2015 | Huntley et al. |
| 2015/0366535 A1 | 12/2015 | Eggers et al. |

FOREIGN PATENT DOCUMENTS

| | | |
|---|---|---|
| CN | 102057296 A | 5/2011 |
| JP | 200023982 A | 1/2000 |
| JP | 2000325347 A | 11/2000 |
| JP | 2001252268 A | 9/2001 |
| WO | WO98/23210 A1 | 6/1998 |
| WO | WO2002/041752 A2 | 5/2002 |
| WO | WO2006/005808 A1 | 1/2006 |
| WO | WO2006/092925 A1 | 9/2006 |
| WO | WO2007/030424 A2 | 3/2007 |
| WO | WO2010/051037 A1 | 5/2010 |
| WO | WO2011/117788 A1 | 9/2011 |
| WO | WO2012/065151 A1 | 5/2012 |
| WO | WO2012/074885 A1 | 6/2012 |
| WO | WO2012/078280 A1 | 6/2012 |
| WO | WO2012/146823 A1 | 11/2012 |
| WO | WO2013/031138 A1 | 3/2013 |

OTHER PUBLICATIONS

American College of Radiology; BI-RADS® ATLAS and MQSA: Frequently Asked Questions; (Revised Aug. 11, 2011), http://www.acr.org/SecondaryMainMenuCategories/quality_safety/BIRADSAtlas/BIRADSFAQs.aspx.

Berg et al.; Mammography vs. mammography alone in women at combined screening with ultrasound and elevated risk of breast cancer; JAMA; 299(18); pp. 2151-2163; May 2008.

Bollmann et al.; Integration of static and dynamic scene features guiding visual attention; Paulus E.; Wahl, F.M.(eds.): Mustererkennung; Berlin et al. (Spinger); pp. 483-490; (year of pub. sufficiently earlier than effective US filing date and any foreign priority date) 1997.

Hughes et al.; Volume estimation from multiplanar 2D ultrasound images using a remote electromagnetic position and orientation sensor; Ultrasound in medicine & biology; 22(5); pp. 561-572; (year of pub. sufficiently earlier than effective US filing date and any foreign priority date) 1996.

IARC (Intl. Agency for Research on Cancer) Handbooks of Cancer Prevention; vol. 7; Breast Cancer Screening; Lyon, France; IARC Press; 243 pgs.; Mar. 2002.

Kaplan, S.; Clinical utility of bilateral whole-breast US in the evaluation of women with dense breast tissue; Radiology; 221(3); pp. 641-649; Dec. 2001.

Kelly et al. fBreast cancer detection using automated whole breast ultrasound and mammography in radiographically dense breastsf, Eur Radiol (Mar. 2010) 20(3): 734R742.

National Cancer Institute; Cancer Rate (per 1,000 examinations) and Cancer Detection Rate (per 1,000 examinations) for 1,960,150 Screening Mammography Examinations from 2002 to 2006 by Time (months) Since Previous Mammography R based on BCSC data as of 2009; BCSC, National Institute of Health; Nov. 15, 2011.

Pazo-Alvarez et al.; Automatic detection of motion direction changes in the human brain, European Journal of Neuroscience, vol. 19(7), pp. 1978-1986, Apr. 2004.

US Dept. of Health and Human Services; Comparative Effectiveness of Core-Needle and Open Surgical Biopsy for the Diagnosis of Breast Lesions; Agency for Healthcare Research and Quality; AJRQ Publication No. 10-EHC007-EF; Dec. 2009.

Crystal et al.; Accuracy of sonographically guided 14-gauge coreneedle biopsy: results of 715 consecutive breast biopsies with at least two-year follow-up of benign lesions.; J Clin Ultrasound; 33(2); pp. 47-52; Feb. 2005.

Duffy et al.; Tumor size and breast cancer detection: What might be the effect of a less sensitive screening tool than mammography?; The Breast Journal; 12(1); pp. S91-S95; Jan.-Feb. 2006.

Jobe, W.E.; Historical Perspectives; in Parker et al. Percutaneous Breast Biopsy; New York; Raven Press; pp. 1-5; Aug. 1993.

Kolb et al.; Occult cancer in women with dense breasts: detection with screening US—diagnostic yield and tumor characteristics; Radiology; 207(1); pp. 191-199; Apr. 1998.

Read et al.; Restoration of motion picture film. Conservation and Museology. Gamma Group. Butterworth-Heinemann. pp. 24R26. ISBN 075062793X; Sep. 11, 2000.

Shapiro et al.; Ten to fourteen-year effect of screening on breast cancer mortality; J Natl Cancer Inst; 69(2); pp. 349-355; Aug. 1982.

Tabar et al.; Mammography service screening and mortality in breast cancer patients: 20-year follow-up before and after introduction of screening; The Lancet; 361(9367); pp. 1405-1410; Apr. 26, 2003.

Tabar et al.; The Swedish Two-County Trial twenty years later: updated mortality results and new insights from long-term follow-up; Radial Clin North Am; 38(4); pp. 625-651; Jul. 2001.

Thompson et al.; Enhancing mental readiness in military personnel. In human dimensions in military operations military leaders' strategies for addressing stress and pschological support; Meeting proceedings RTO-MP-HFM-134; Brussels, Belgium; pp. 4-1 thru. 4-12; Apr. 2006.

Eggers et al.; U.S. Appl. No. 14/787,856 entitled "Hand-held imaging devices with position and/or orientation sensors for complete examination of tissue," filed Oct. 29, 2015.

Robinson et al. et al.; U.S. Appl. No. 14/900,468 entitled "Image recording system," filed Dec. 21, 2015.

Eggers et al.; U.S. Appl. No. 15/635,111 entitled "Method, apparatus and system for complete examination of tissue with hand-held imaging devices," filed Jun. 27, 2017

* cited by examiner

Reference Planes
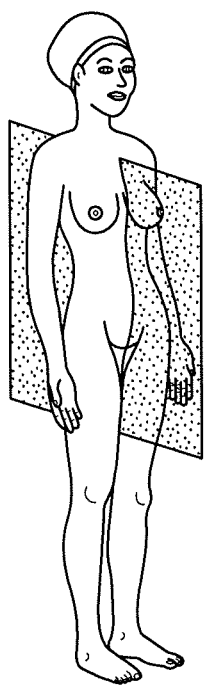 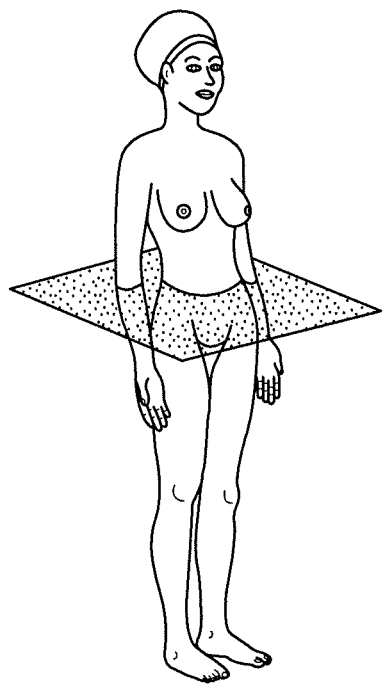 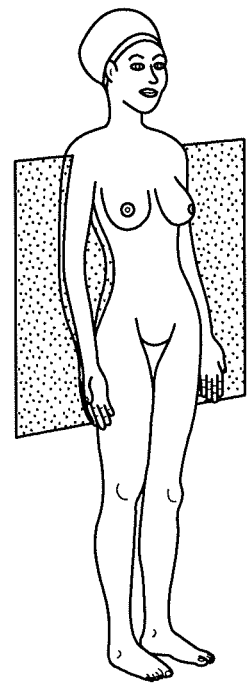
Sagittal plane (median plane)  Transverse plane (horizontal plane)  Coronal plane (frontal plane)
FIG. 2

Transforming Actual Tissue Geometry to Match Idealized Tissue Geometry: Correction to the Body's Coronal Plane

Transforming Actual Tissue Geometry to Match Idealized Tissue Geometry: Correction of Breast Size (Pendulous Extension) to Hemispherical Profile

Depicting Lesion Location With Polar Coordinates
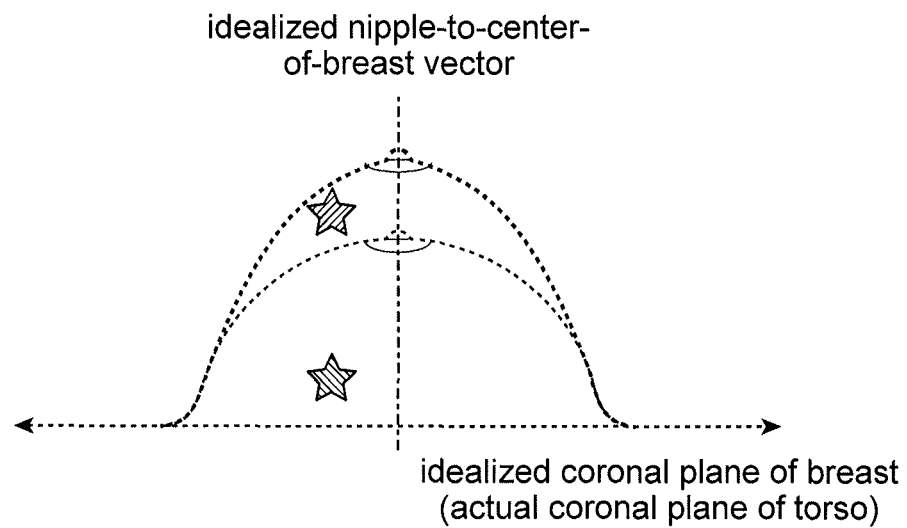
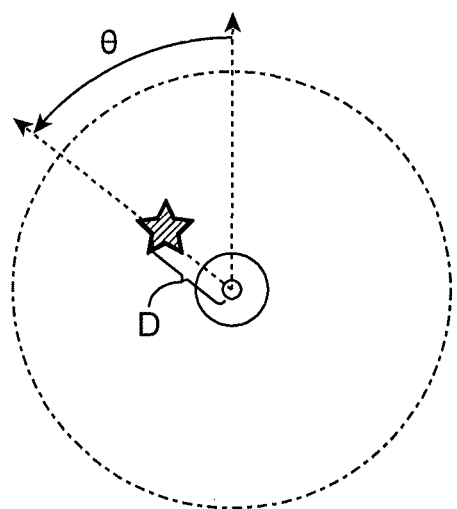
FIG. 5

Reconstructing Coverage Sections on Idealized Structure Indicates Extent of Coverage

Overlapping Sections to Ensure Complete Coverage

Variable Breast Sizes Mapped to a Standard Map
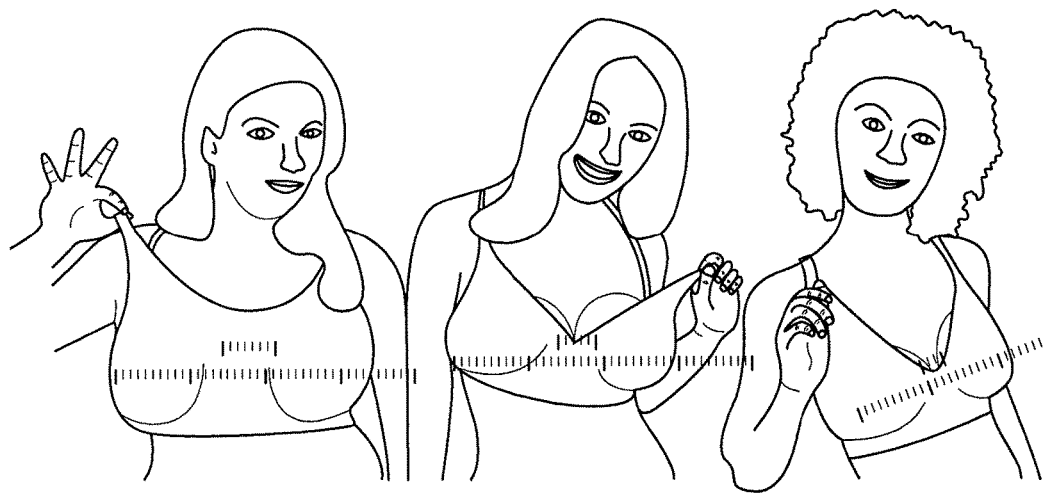
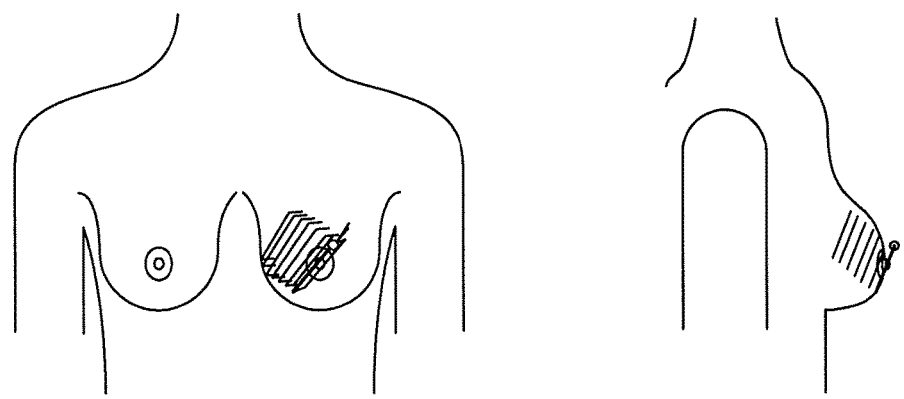
FIG. 18

Actual and Idealized Lesion Location When Patient is on Back

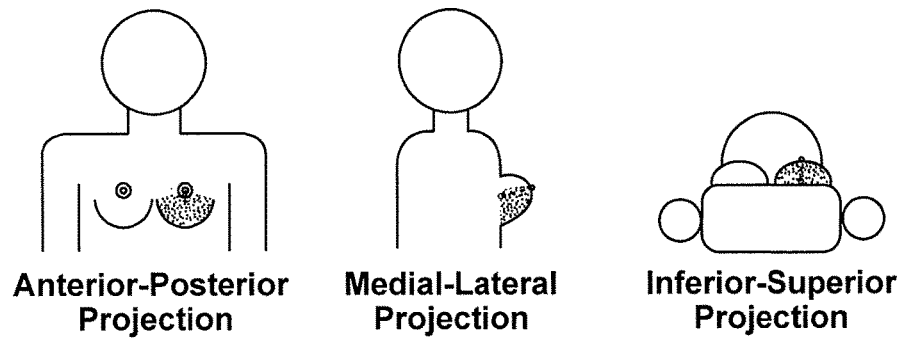

Anterior-Posterior Projection    Medial-Lateral Projection    Inferior-Superior Projection

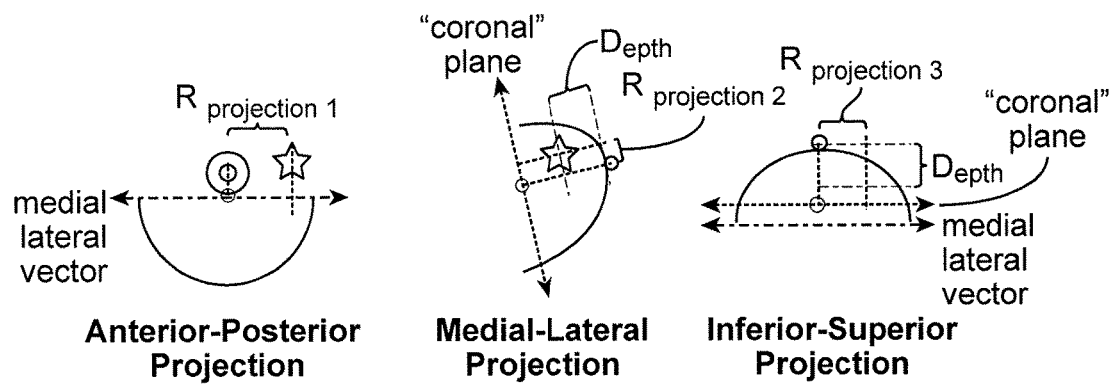

Anterior-Posterior Projection    Medial-Lateral Projection    Inferior-Superior Projection

Actual Scan Spatial Geometry

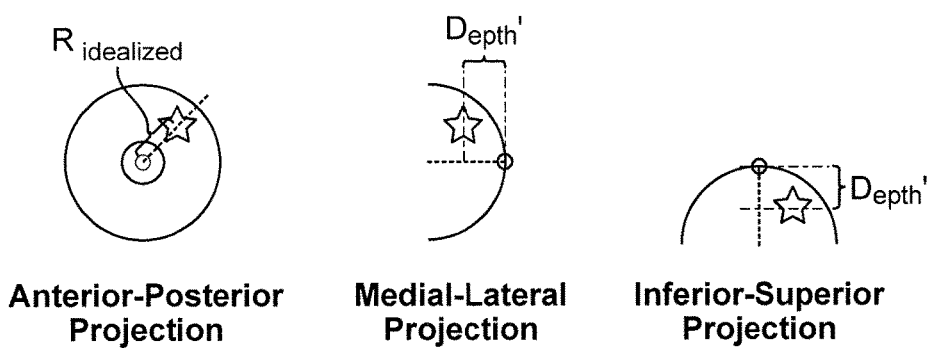

Anterior-Posterior Projection    Medial-Lateral Projection    Inferior-Superior Projection

Reconstructed and Idealized Scan Spatial Geometry

FIG. 23

Variances in Absolute Mapping of the Same Feature Resulting From Differences in Scan Pattern or Differences in Reference Geometries

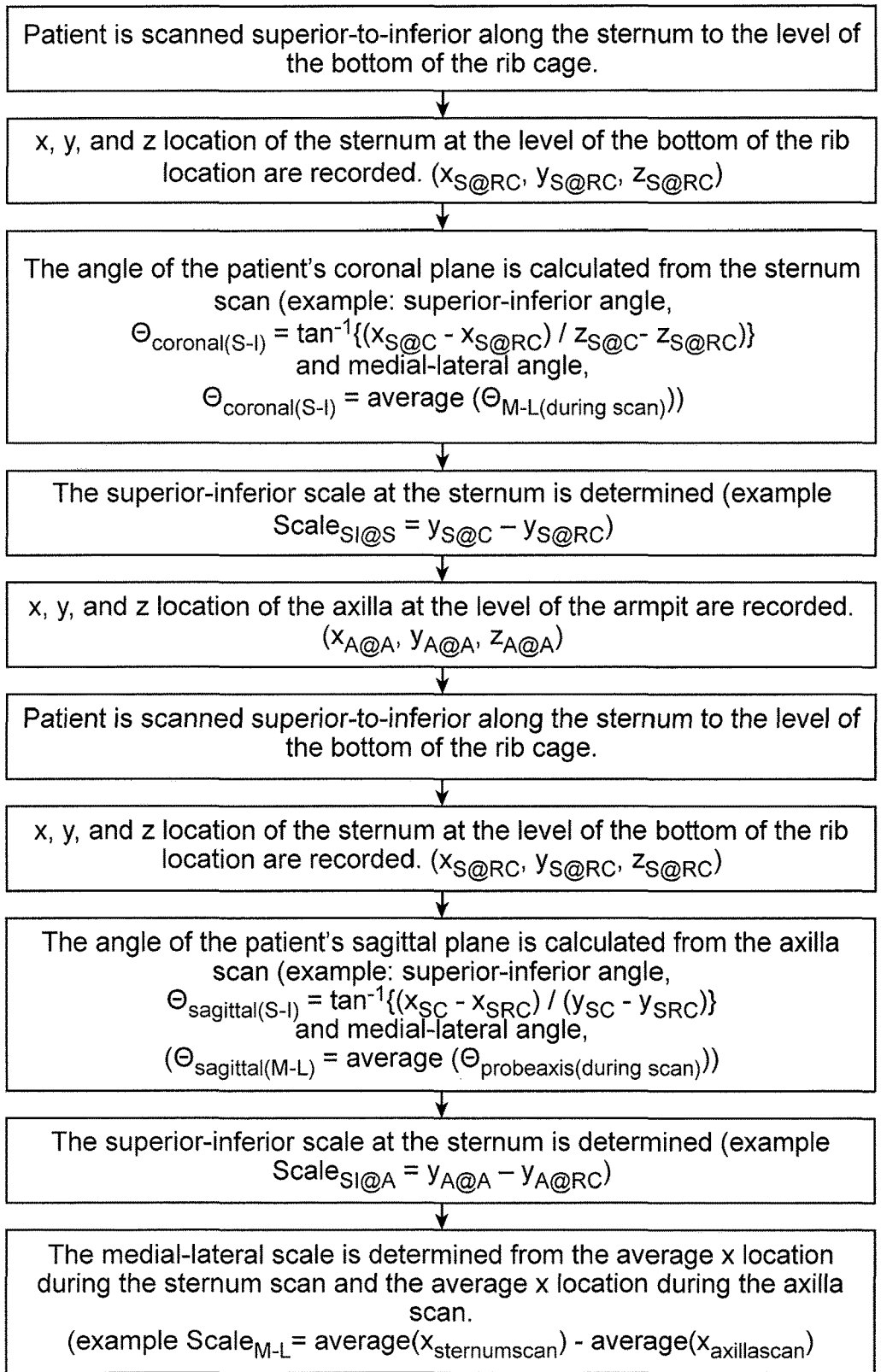
FIG. 27 (Cont. 1)

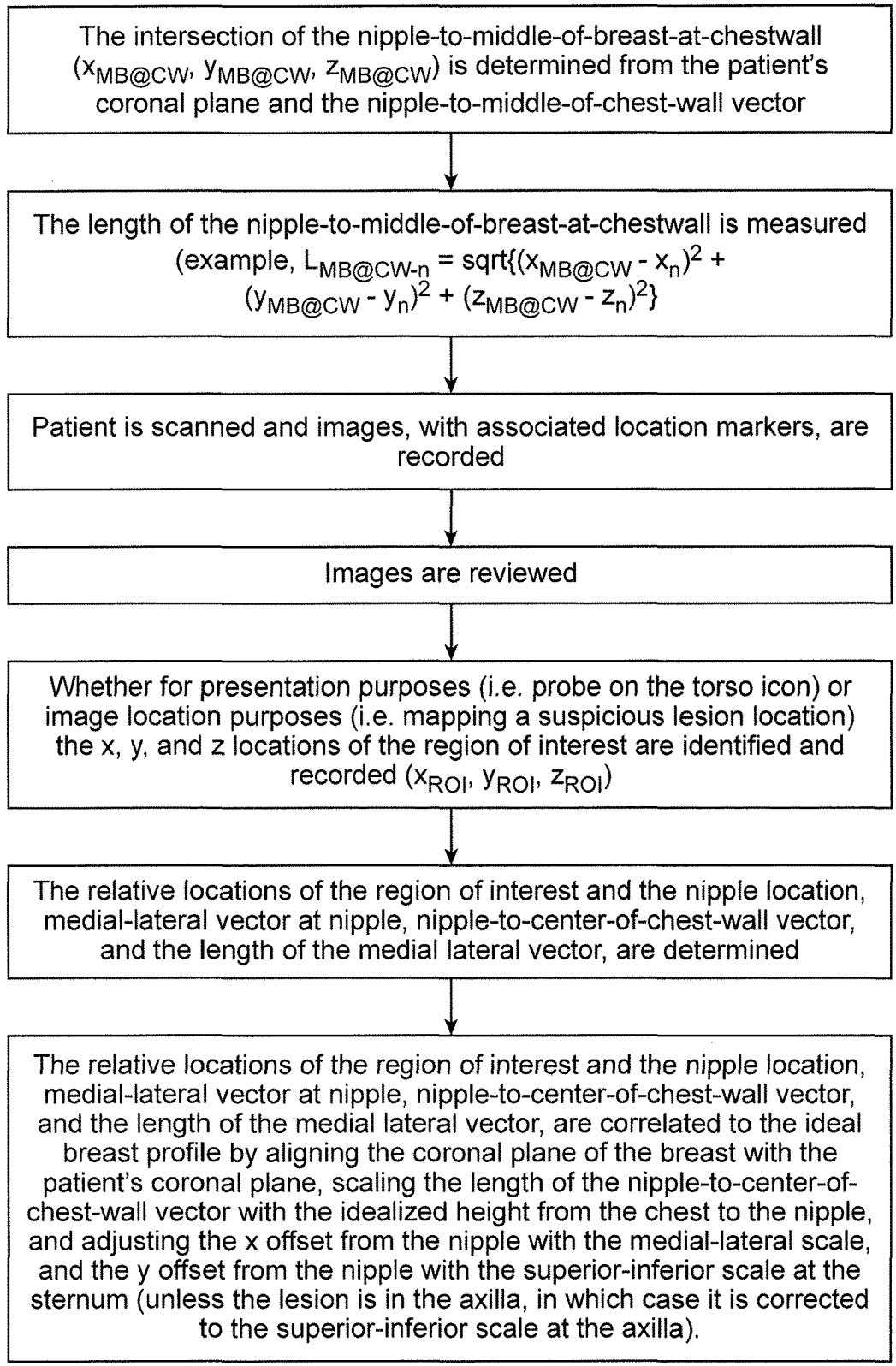
FIG. 27 (Cont. 2)

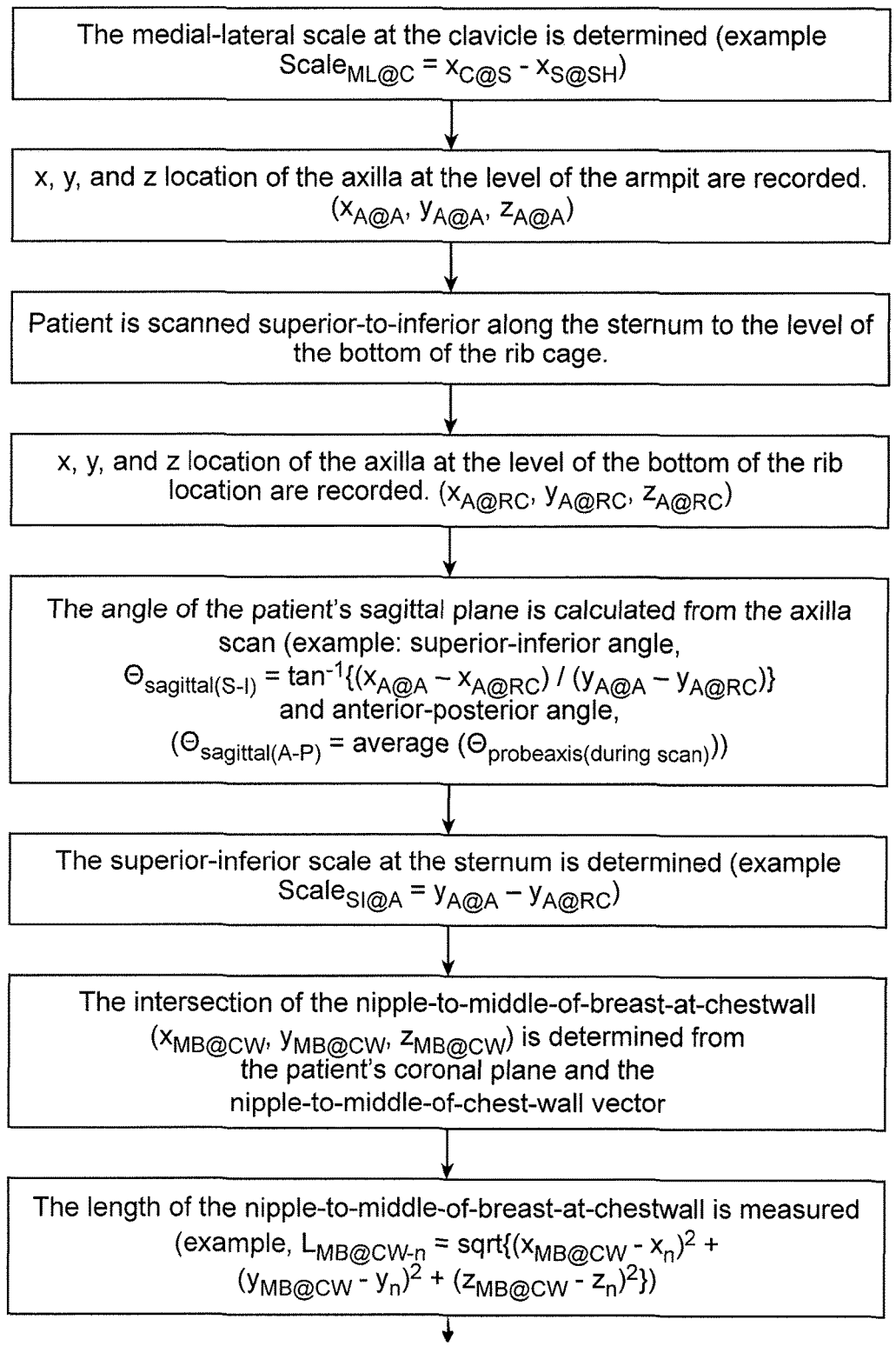
FIG. 28 (Cont. 1)

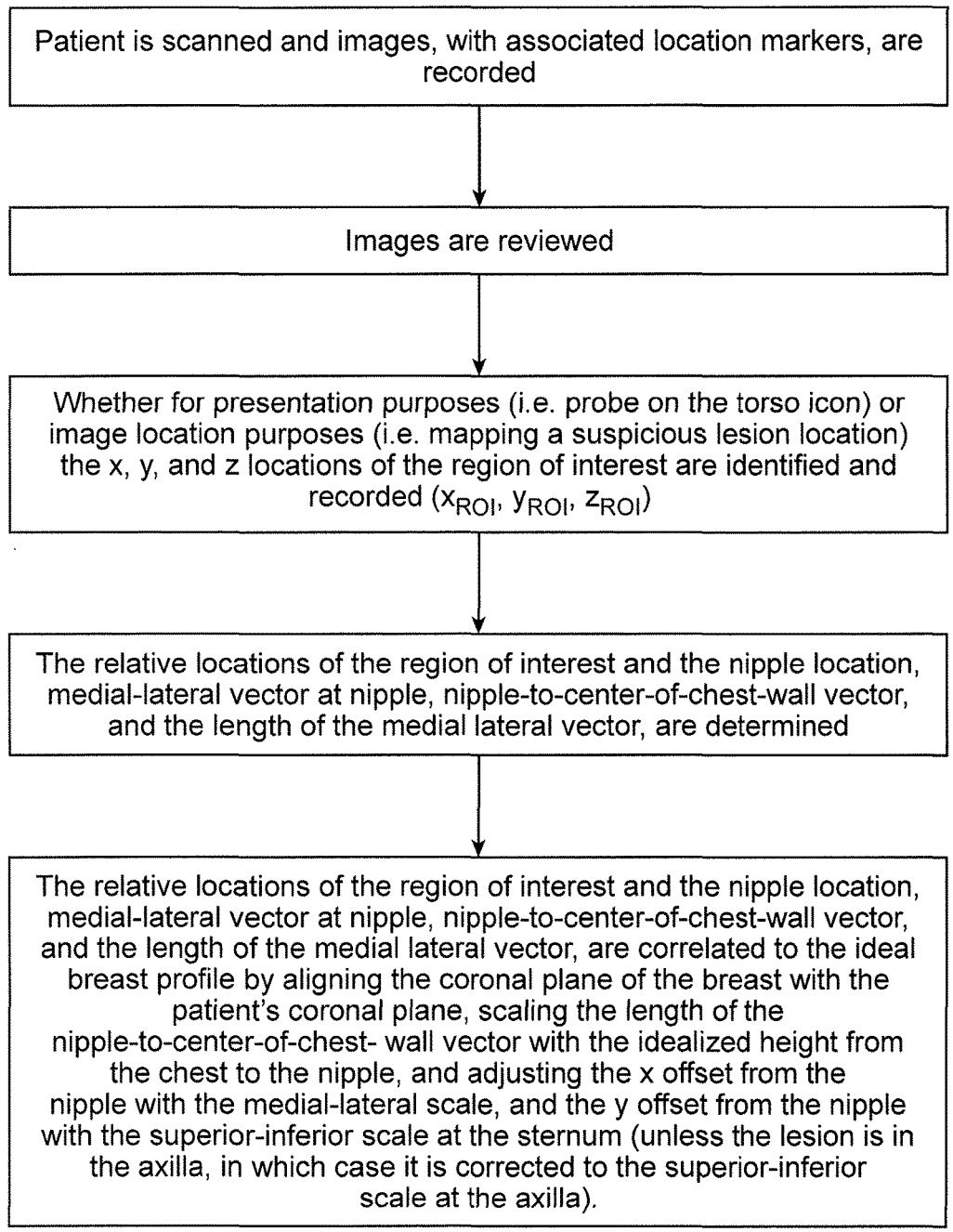
FIG. 28 (Cont. 2)

SYSTEMS AND METHODS FOR TISSUE MAPPING

CROSS REFERENCE TO RELATED APPLICATIONS

This application claims the benefit of U.S. Patent Appl. No. 61/840,277, filed Jun. 27, 2013, the disclosure of which is incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

FIELD

Described herein are various embodiments of tissue mapping systems and methods of using such systems to map features in actual tissue onto idealized images.

BACKGROUND

Mapping, by definition, requires describing the relative location of features, with respect to each other, and mapping medical images obtained by a medical examination requires that location of identifiable tissue structures be described relative to other tissue features. Traditionally, scanning devices have immobilized the patient and moved the scanning device around that immobilized patient, or moved the immobilized patient through the scanning device on a carrier. In the specific example of breast imaging examples of these methods are (1) mammography, where the patient's breast is compressed between two paddles so that it cannot move and an external x-ray imaging source takes images of the breast from one or more angles. In the case of magnetic resonance imaging (MRI) the patient lies prone (on her stomach) on a sort of stretcher and her breasts extend pendulously through holes in that stretcher, and the entire stretcher structure is moved through the MRI imaging device. Even if several images are taken over a sustained period of time, the breast structure does not move and the relative position of one structure to another does not change.

When imaging a structure that is not immobilized, particularly when imaging an inherently mobile structure, such as the female human breast, and even more particularly when imaging that mobile structure with a plurality of images that are obtained at different moments in time, the challenge of mapping the location of one tissue structure relative to another requires a different perspective.

Methods, devices, and systems are disclosed herein to address the challenges associated with mapping the relative locations of mobile tissue structures.

SUMMARY OF THE DISCLOSURE

Methods, apparatus, and systems for use with an ultrasound imaging console in screening a volume of tissue are disclosed herein. The targeted human tissue can include a human breast.

In general, in one embodiment, a tissue mapping and imaging system includes an image recording and mapping system in communication with a manual image scanning device having an imaging probe. The manual image scanning device is configured to scan a volume of tissue and output at least one scanned image. The image recording and mapping system is configured to electronically receive and record the at least one scanned image, and the image recording and mapping system is configured to construct an idealized tissue map from the at least one scanned image. A position tracking system is configured to detect and track the position of the imaging probe and provide location identifier information for the at least one scanned image. The position tracking system can be configured to electronically output probe position data and the location identifier information to the image recording and mapping system.

The image recording and mapping system can be configured to correlate a recorded position for a tissue feature in a recorded image with an idealized position for the tissue feature in the idealized tissue map. The idealized tissue map can be an idealized depiction of the anatomy. The image recording and mapping system can be configured to align a recorded tissue feature in the at least one scanned image with an idealized tissue feature in the idealized tissue map. The idealized tissue feature can be a reference point. The image recording and mapping system can be configured to align a recorded geometry of the at least one scanned image with an idealized geometry of the idealized tissue map. The position tracking system can comprise a plurality of position sensors coupled to the imaging probe, and the position sensors can be configured to provide data corresponding to the position of the imaging probe. The position tracking system can comprise at least one receiver configured to receive the position data from the sensors. The system can further include microwave position sensors. The image recording and mapping system can be configured to identify at least two reference marks in the tissue based on the position and location information received from the position tracking system. The image recording and mapping system can be configured to identify a coronal plane for the tissue based on the position and location information received from the position tracking system. The image recording and mapping system can be configured to identify a sagittal plane for the tissue based on the position and location information received from the position tracking system. The image recording and mapping system can be configured to scale the at least one scanned image to the idealized tissue map based on the position and location information received from the position tracking system. The image recording and mapping system can be configured to identify a medial-lateral scale based on the position and location information received from the position tracking system. The image recording and mapping system can be configured to translate a recorded position for a region of interest in the at least one scanned image to a corresponding position on the idealized tissue map. The image recording and mapping system can be configured to perform the steps of identifying a plane of the scanned tissue, identifying a first anterior-posterior projection through a tissue reference point to the identified plane, identifying a second anterior-posterior projection through a probe reference point to the identified plane, computing a relative angle between the first and second projections and medial-lateral vector through the tissue reference point, computing a distance between the first and second projections, and constructing the idealized map based on the relative angle and distance computed. The image recording and mapping system can be configured to perform the steps of determining a position of a region of interest in the scanned tissue volume relative to at least one of the identified projections, computed angle, or computed distance, and depicting the region of interest on the idealized tissue map in an idealized position based on the position of the region of interest determined relative to at least one of the identified projections, computed angle, or computed distance. The image recording and mapping system can be configured to translate a recorded position of a region of interest in the at least one scanned image to a corresponding position in the idealized tissue map. The tissue volume can be a patient's breast and the image recording and mapping system can be configured to perform the steps of identifying a relative coronal plane of the breast, identifying a nipple-to-middle-of-chest-wall vector, identifying medial and lateral boundaries, identifying superior and inferior boundaries, identifying a sagittal plane for the tissue volume, identifying a patient's coronal plane, and identifying a patient's medial-lateral alignment. The image recording and mapping system can be configured to scale a medial-lateral location of a region of interest to fit the idealized tissue map based on information from the position tracking system. The image recording and mapping system can be configured to scale a superior-inferior location of a region of interest to fit the idealized tissue map based on information from the position tracking system during the lateral and medial scans.

In general, in one embodiment, a tissue mapping system includes a recording system including a controller in communication with a manual image scanning device. The controller is configured to electronically receive and record the scanned images from the manual image scanning device, and to correlate recorded position of a region of interest to an idealized position of the region of interest on an idealized depiction of the anatomy. A position tracking system can further include at least one position and/or orientation sensor configured to provide data corresponding to the position and/or three-dimensional orientation of the manual image scanning device.

The controller can be configured to determine a differential angle of a patient's coronal plane with reference to a plane of the floor. The controller can be configured to determine a differential angle of a patient's arm with reference to a patient's transverse plane. The controller can be configured to append location identifier information to the scanned images from the manual image scanning device. The image recording and mapping system can be configured to scale a medial-lateral location of a region of interest to fit the idealized depiction based on information from the position tracking system. The controller can be configured to scale a superior-inferior location of a region of interest to fit the idealized depiction based on information from the position tracking system during the lateral and medial scans.

In general, in one embodiment, a method of constructing an idealized representation of a patient's scanned breast includes:

(1) recording a scanned image of the patient's breast;

(2) conforming the geometry of the recorded image to an idealized geometry for an idealized breast map; and (3) depicting a recorded tissue feature in the idealized breast map by translating the recorded position of the tissue feature in the scanned image to a corresponding position in the idealized breast map.

The method can further include generating position data for the scanned image from a plurality of sensors, electronically communicating the position data from the plurality of sensors to a tissue map processor. Based on the position data the processor can identify a coronal plane for the patient, a first anterior-posterior projection through a tissue reference point to the coronal plane, and a second anterior-posterior projection through a probe reference point to the coronal plane. The method can further include computing a relative angle between the first and second projections and medial-lateral vector through the tissue reference point, computing a distance between the first and second projections, and constructing the idealized map based on the relative angle and distance computed. The processor can be configured to identify a relative coronal plane of the breast, a nipple-to-middle-of-chest-wall vector, medial and lateral boundaries, superior and inferior boundaries, a sagittal plane for the patient, a coronal plane for the patient, and a medial-lateral alignment for the patient. The method can further include scaling the scanned image to the size and shape of the idealized map. The processor can be configured to apply trigonometric reconstruction to generate the idealized map. The processor can be configured to apply geometric reconstruction to generate the idealized map.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 2 illustrates various planes of a human body.

FIG. 5 illustrates lesions on models of a human breast.

FIG. 18 illustrates examples of variable breast sizes mapped to a standard tissue map in accordance with some embodiments.

FIG. 23 illustrates various views of a lesion mapped on the actual scan spatial geometry and idealized scan spatial geometry when the patient is on their back in accordance with some embodiments.

DETAILED DESCRIPTION

Methods, devices, and systems are disclosed herein that can be used with manual imaging techniques to improve mapping of a portion of a human anatomy, such as a female human breast. Imaging a movable structure can be challenging when using multiple scans to image and map the anatomy. The methods, devices, and systems disclosed herein can be used with an ultrasound imaging probe and console to improve the mapping of the body tissue, such as the female human breast.

The female human breast is often thought of as being hemispherical or conical and protruding from the chest with the nipple pointing straight upward (anterior). The projection of the nipple on the middle of the breast at the chest wall (coronal plane, A in FIG. 1) is directly posterior of the nipple (B in FIG. 1). This, in fact, is almost never the actual case. Gravity causes the breast to move so that the nipple is almost always offset from the middle of the breast at the chest wall.

Most "maps" of the breast, however, depict an idealized breast. A lesion which is upper and outer from the nipple (for example, at the 10:30 position on the right breast), but is close to the chest wall (C in FIG. 1), but a lesion which is upper and outer from the nipple on that same breast, but close to the nipple (D in FIG. 1) may be, because the entire breast is offset from the true anterior posterior axis, at a different location, relative to the center of the breast on the chest wall. If the breast were physically lined up on the true anterior-posterior axis, as is the case in the ideal mapping presentation, they might appear to be one-behind-the-other.

Figure 1:
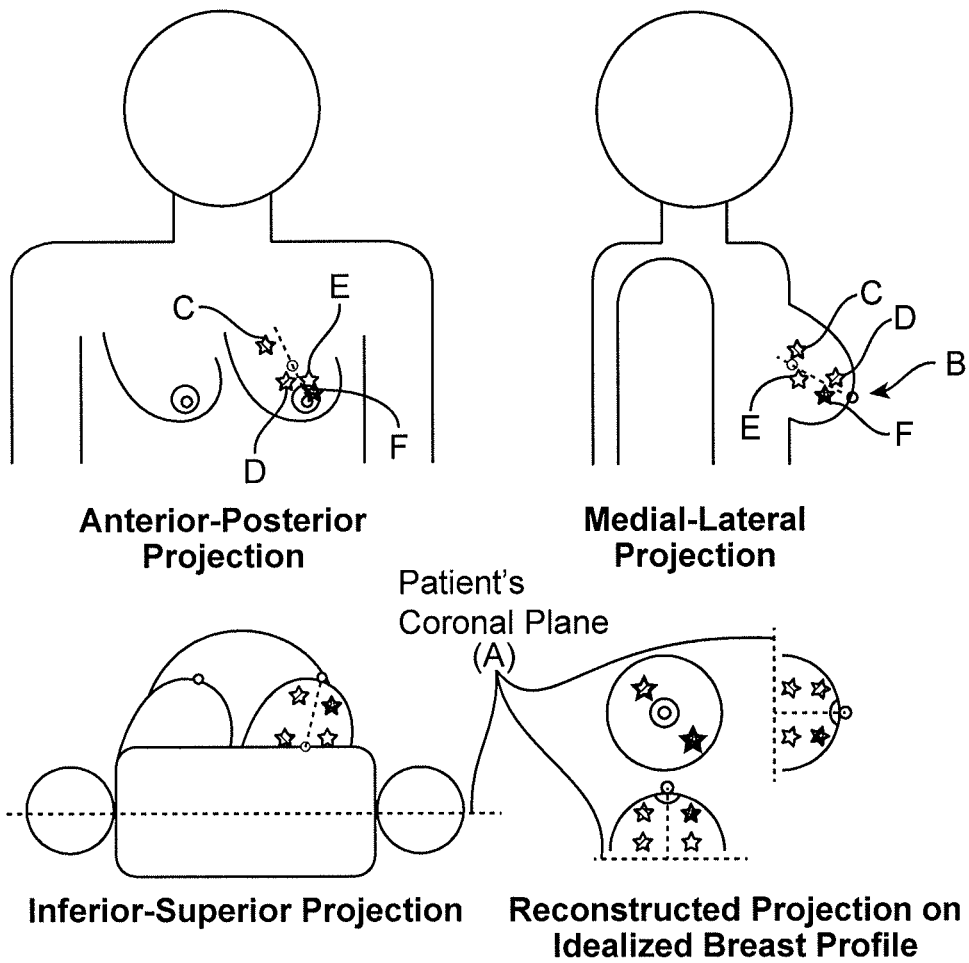
FIG. 1 is an illustration of various views of a female human body and breast.

Referring to FIG. 1, in the shown breast orientation, the superior part of the breast is extended and the inferior part of the breast is compressed. Thus, the 10:30 lesions described in the previous paragraphs describe lesion which are at the same "o'clock" position and the same "radius" from the nipple-to-center-of-breast vector. The relative depth, from the nipple, is extended from what it would be in the ideal breast profile. Thus the depiction in the ideal construction/reconstruction shows those lesions closer to each other than they are actually measured on the ultrasound images. As another example, if there were two lesions on the contra-side of the nipple-to-center-of-breast vector (E and F at 4:30), and the same depth, if the breast were oriented straight out from the coronal plane, as the two lesions on the 10:30 side, they would be compressed along with the rest of the breast. Therefore, the measured distance between the two lesions would be closer than that measured by the ultrasound device.

In order to construct an "ideal" breast for mapping purposes (that is, a breast with the nipple protruding from the chest wall with the nipple directly anterior to the center of the breast on the chest wall), it is important to be able to map the features from the actual breast (or tissue) onto an idealized image with some degree of spatial correspondence. For example, when scanning breast tissue, the generated scanned image may show a suspicious lesion at a position that is relative to a reference (such as the nipple) on the breast tissue while the breast tissue is in a non-idealized and/or imaged orientation. When this lesion is then mapped onto an idealized breast image, the placement of the suspicious lesion on the idealized image should correspond to some degree with the location of the lesion in the scanned imaged orientation. This provides the user with a sense of where the lesion is positioned in the actual breast relative to the reference point.

To address this challenge, embodiments described herein provide for methods and systems using location identification information for the actual orientation of the scanned breast to depict the features of the scanned breast onto the idealized image. Additional embodiments described herein align or otherwise modify the images of the actual breast orientation to conform to an idealized breast. For example, some embodiments reconstruct an "ideal" breast for mapping purposes by determining the orientation of the axis of the vector from the nipple to the center of the breast at the chest wall, so that the vector, and the location of features relative to that vector, may be adjusted to a true anterior posterior orientation.

Another additional aspect describes a device and method for obtaining a reference point from which to measure all other image structures within an image set, such set being obtained over a period of time, and using that reference to map those image structures relative to each other. Further embodiments will be described in greater detail herein.

A. Coronal and Sagittal Projections of the Transverse Image

As shown in FIG. 2, when describing the relative position of structures within the body they are generally referenced off of three, orthogonal planes: (1) the sagittal plane (a plane which is parallel to the plane that runs through the middle of the body separating the eyes, breasts, legs, etc). The sagittal planes that are closer to the middle of the body are medial and the sagittal planes that run closer to the outside of the body are lateral; (2) a transverse plane which is parallel to the plane that runs through the middle of the body, bisecting the top (superior) and bottom (inferior) sections; and (3) the coronal plane, (a plane which is parallel to the plane which runs through the middle of the body separating the front (anterior) and back (posterior) parts of the body).

Some embodiments provide for systems and methods of displaying the three-dimensional image information on the two-dimensional format of the modern electronic radiology workstation. Many tissue structures, particularly the breast, do not directly orient with axial, sagittal, or the axial planes. Since the ultrasound probe is placed on the skin it is common to think of the top row of the image as being the most anterior and the bottom part as being the most posterior. While this is generally correct, it rarely is completely correct. For example, when an ultrasound probe is at the base of the breast near the axilla, and that probe is angled toward the center of the breast (on the chest wall), the "top" row of the image is actually more lateral than anterior and the "bottom" row is more medial than posterior.

Some embodiments provide for systems and methods that display the three-dimensional probe and image location (e.g. ultrasound) by calculating the projection of the probe and image on both the coronal plane (as it runs under the breast, adjacent to the chest wall) and the sagittal plane (as it runs through the middle of the breast, if the breast were oriented such that the nipple was directly above the center of the breast on the chest wall).

1. Idealized Vs Actual Geometry and the Coronal Projection of Features

Because some tissue structures, such as the breast, can be mobile, that is, they can move when the patient is moved, there can be variations in actual vs idealized tissue structure geometry. For instance, referring to FIG. 3, an idealized breast would protrude from the base of the chest wall with the center of the nipple corresponding to the center of the breast on the chest wall, and the Anterior-Posterior vector. Many breasts will offset so that the nipple will not be above the middle of the breast on the chest wall and the vector from the nipple to the middle of the breast on the chest wall will not be parallel to the A-P plane. These variations can be compensated for in order to provide an accurate tissue map.

Figure 3:
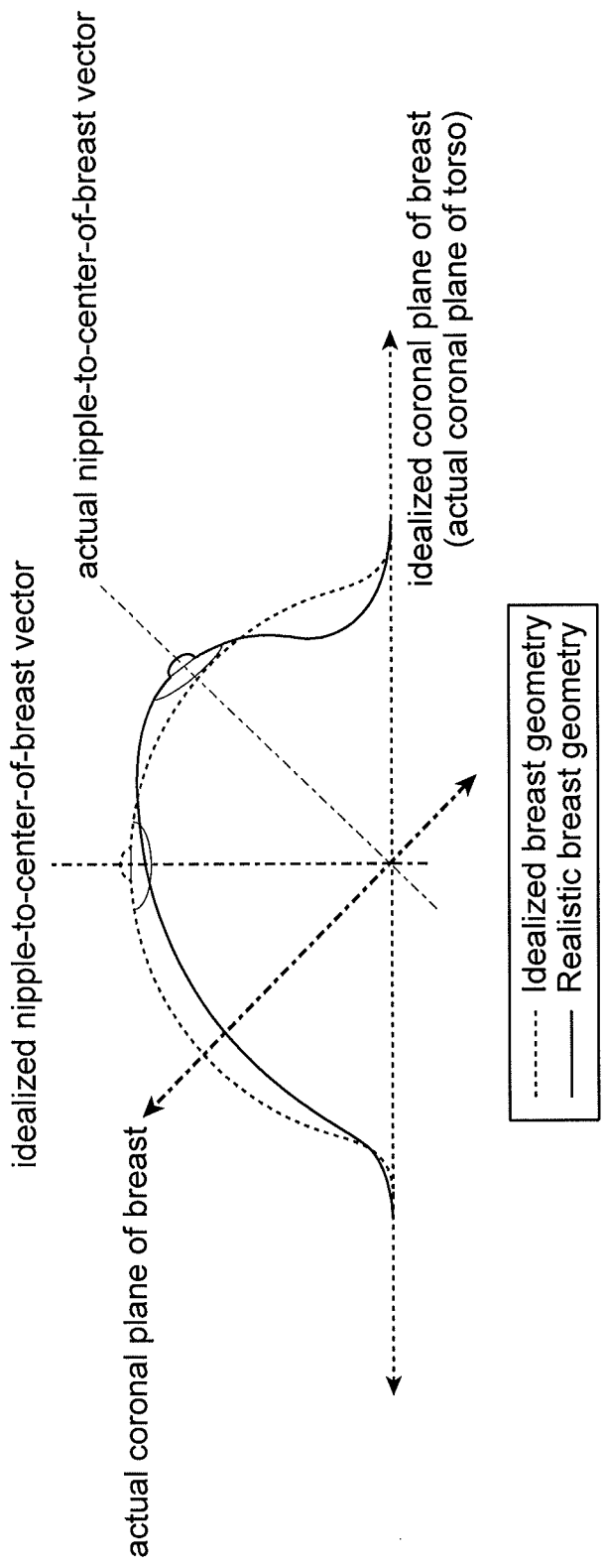
FIG. 3 illustrates examples of an idealized geometry of a human breast versus an example of a realistic geometry of a human breast.

As depicted in FIG. 3, in the idealized breast profile the nipple protrudes from the torso at a 90° angle to the patient's coronal plane. As described above, actual breasts are often mobilized in an orientation that does not conform to the ideal geometry. To conform an image of the actual breast to the ideal geometry, some embodiments, align the actual nipple-to-center-of-breast-(at-chest-wall) vector to correspond to the idealized nipple-to-center-of-breast-(at-chest-wall) vector (see FIGS. 4A-B).

As shown in FIG. 3, the actual coronal plane does not conform to the idealized coronal plane. As referred herein, the term "coronal plane" or "orthogonal plane" may be used broadly to refer to a plane of the patient or tissue that is orthogonal to the actual nipple-to-center-of breast vector. In the case of the non-idealized breast geometry, the actual coronal plane may not be aligned or parallel to the idealized coronal plane.

Figure 4A:
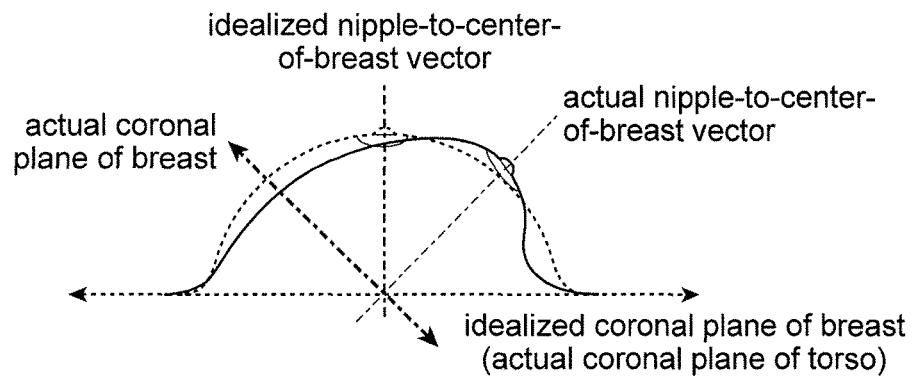
FIGS. 4A-4D illustrate additional examples of an idealized geometry of a human breast versus an example of a realistic geometry of a human breast.
Figure 4B:
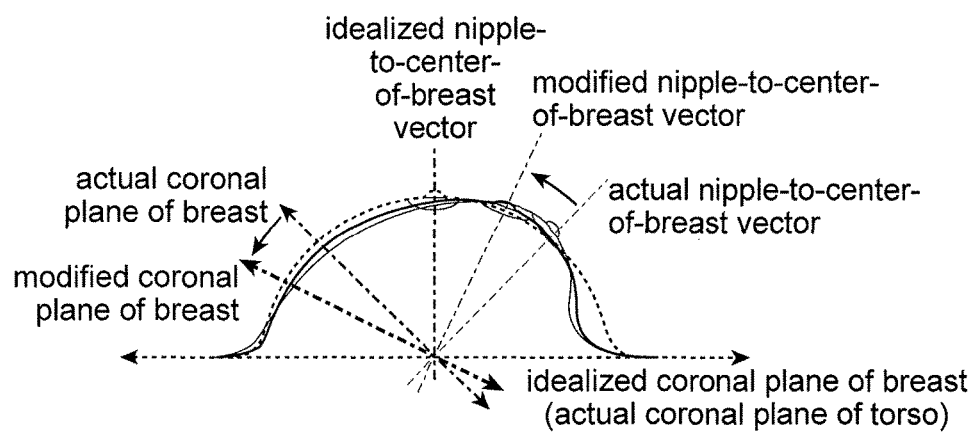

As shown in FIGS. 4A-B, the actual breast geometry provides a vector from the nipple to the middle of the breast on the chest wall that is not parallel with the idealized nipple to center of breast vector. The image of the actual breast is translated, transformed, adjusted, or modified to align the actual and idealized vectors. This may include rotating the image such that the vectors are parallel or overlapping.

Figure 4C:
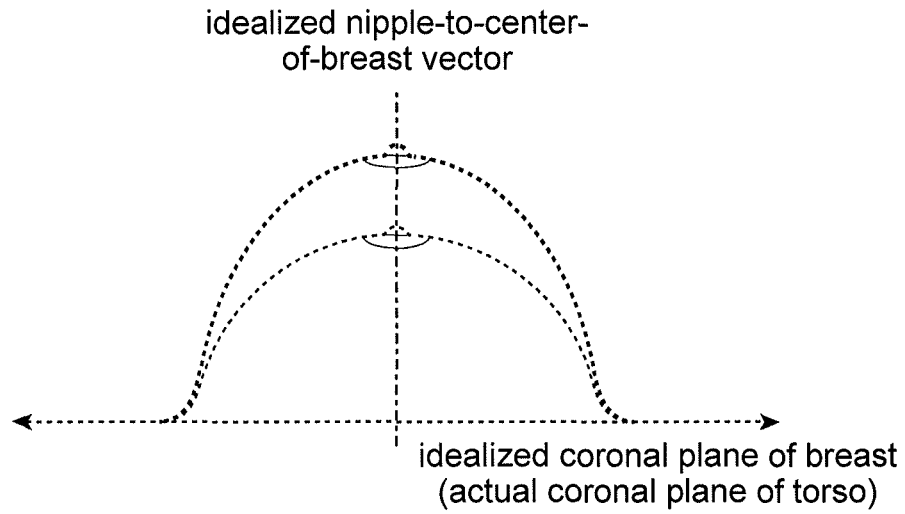
Figure 4D:
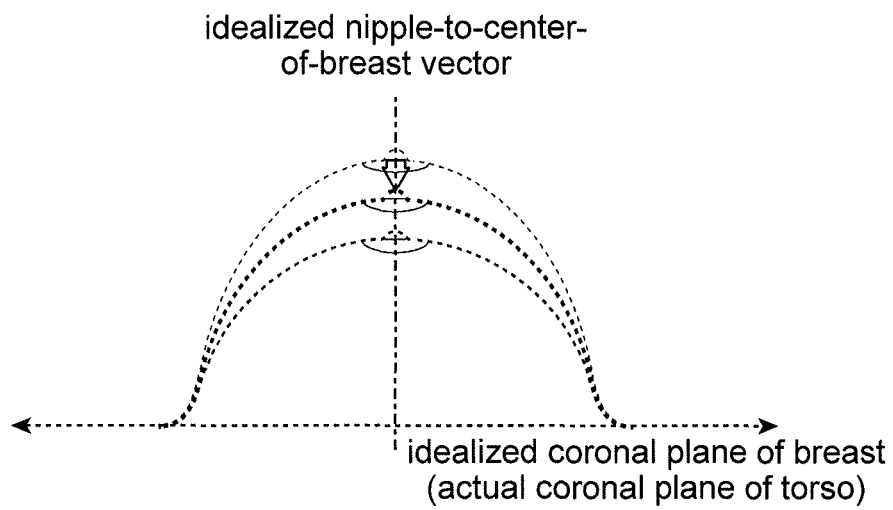

In addition to variations in the angle at which the breast is oriented, the size and shape of different breasts vary. Some breasts are round. Other breasts are conical (pendulous) or flat. The ratio of pendulous extension to breast diameter may not correspond to the idealized profile of a hemisphere. As shown in FIGS. 4C-D, another transformation that can be performed is to conform the pendulous extension to represent the idealized ratio.

Even though the breast is a three-dimensional object, conventional protocol is to present structures in two-dimensional polar coordinates. Those coordinates are described as the radial distance from the nipple-to-center-of-breast-(at-chest-wall) vector (D) and the angular rotation of that radial vector (referenced from a standard vector, such as the top, or 12 o'clock vector (see FIG. 5).

As depicted in FIG. 5, two different breasts may be shaped differently and may have lesions that are located at different depths, but are positioned at the same radial distance (D) from the nipple-to-center-of-breast-(at-chest-wall) vector and may be located on the same vector. Even if these two lesions are at a different depth, they will be described as having the same "location".

Figure 6:
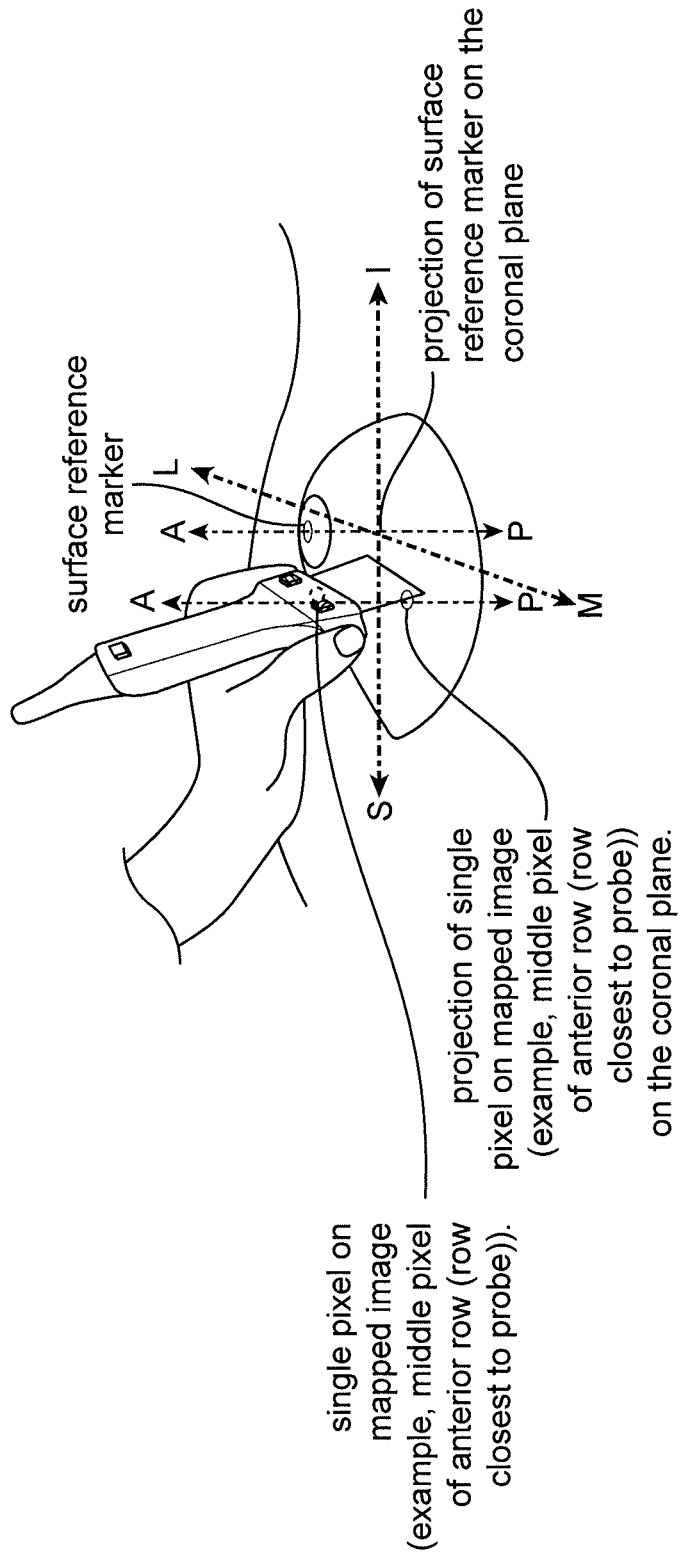
FIGS. 6-7 illustrate images of an imaging probe scanning a human breast in accordance with some embodiments.

An example of this is provided in FIG. 6. The ultrasound probe is placed on the medial (M) portion of the left breast, superior to the nipple. The probe is held at a slight angle, oriented such that the bottom row of the image, the deeper part of the image, is more inferior (I) than the more superior (S) shallower part of the image. If the breast were not mobile, then an anterior (A)-posterior (P) vector through the nipple would project the center of the breast on the coronal plane at the chest wall. An AP vector through the middle of the probe projects the point representing the middle of the probe on coronal plane at the chest wall.

Figure 7:
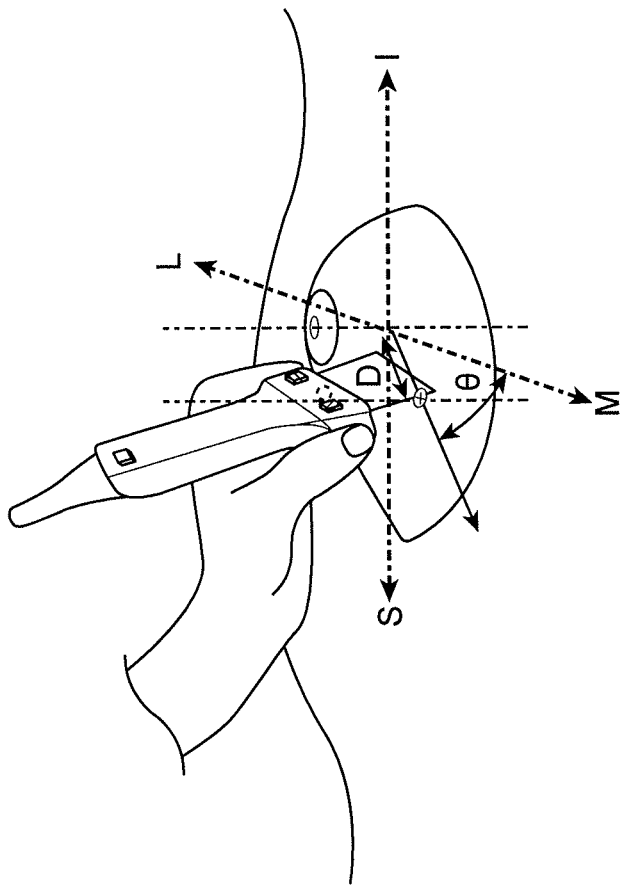

The coronal projection of that middle point may be "mapped" by the angle ($\theta$) between the vector of that point to the reference point (nipple projection on coronal plane) and the medial-lateral (M-L) vector through the reference point and the distance (D) of that point from the reference point as shown in FIG. 7. The distance (D) is not the distance along the skin from the nipple, but the distance from the coronal projection of the nipple to the coronal projection of the point.

Figure 8:
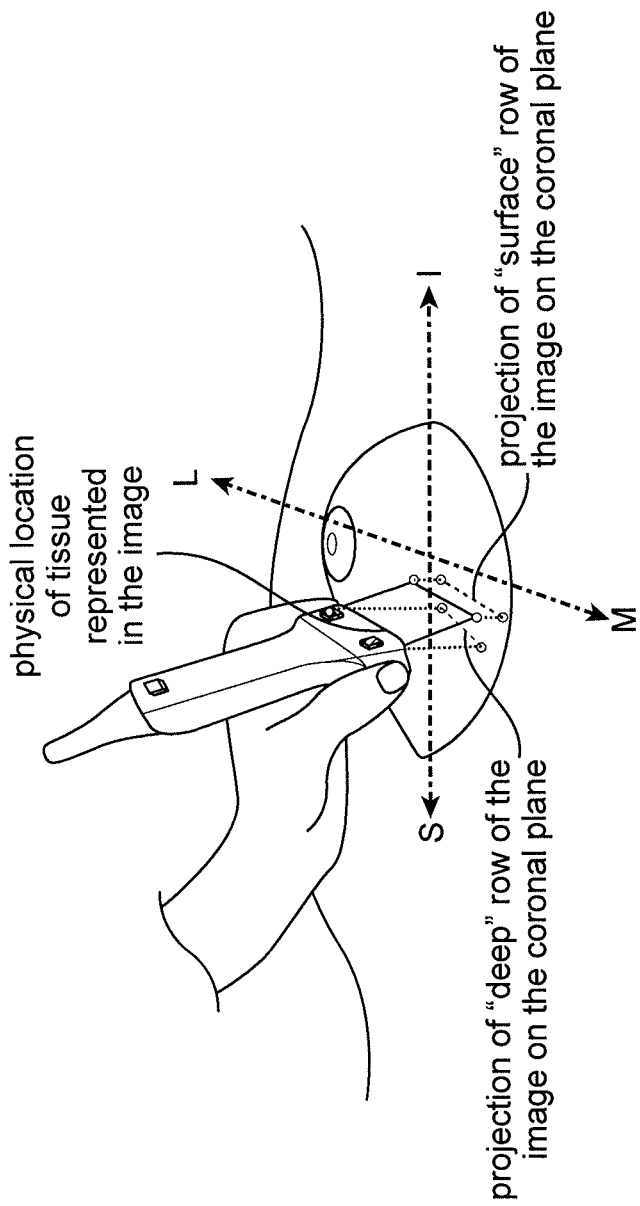
FIG. 8 illustrates the location of a scan image relative to the geometry of a human breast in accordance with some embodiments.

As shown in FIG. 8, if A-P vectors were projected through the four corners of the image, two "lines" would appear, representing the coronal projection of the "top" row (row closest to the skin) and the "bottom" row (row furthest from the skin).

Figure 9:
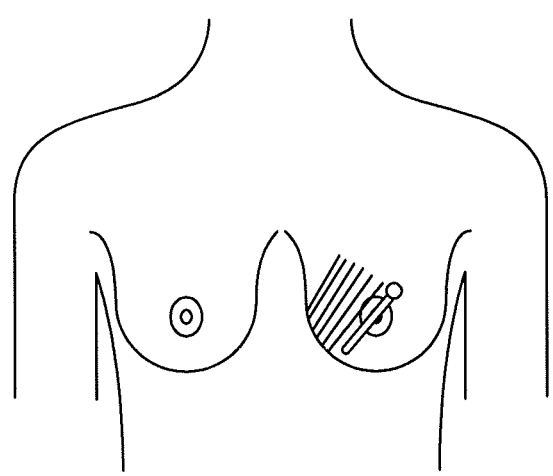
FIGS. 9 and 11 illustrate a coronal projection of the tissue map.

In some embodiments, the tissue mapping system described displays the coronal projection of the top row (adjacent to skin) of the current probe location along with a history of the recorded images, also presented as coronal projections of the top row, on a forward-facing idealized torso (FIG. 9).

Figure 10:
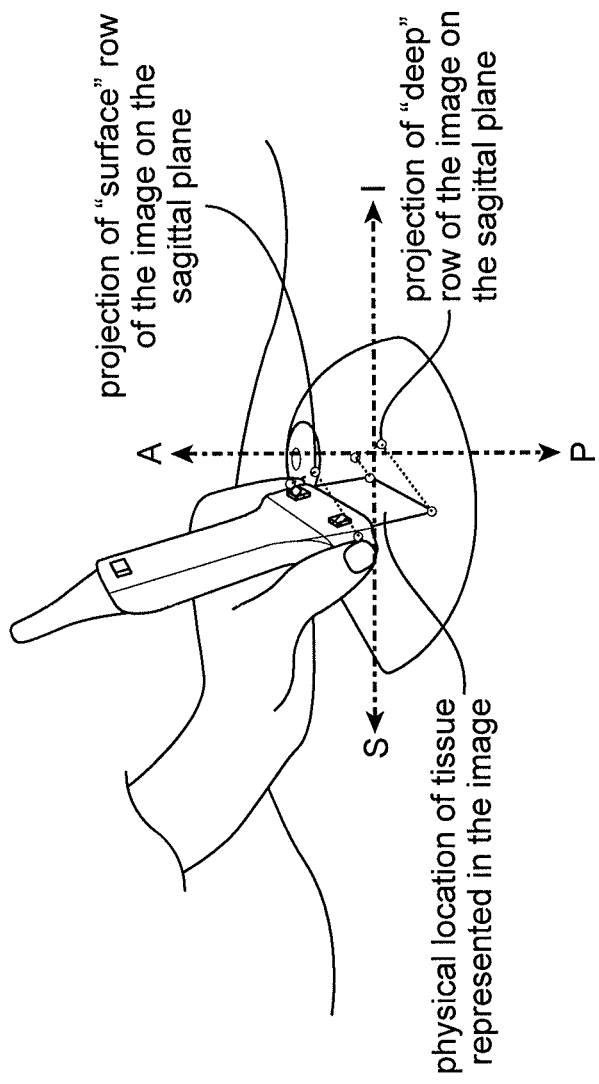
FIG. 10 illustrates coronal projections of the top and bottom image rows of the scanned image.
Figure 11:
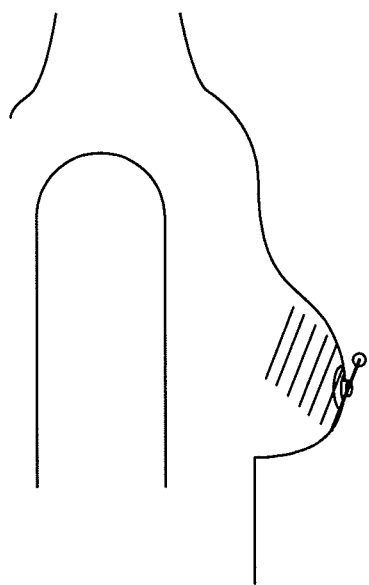

In some embodiments, in order to present the image map locations in three dimensions, the image is also projected onto the sagittal plane (see FIG. 10). As shown in FIG. 11, the tissue mapping system contemplated displays the sagittal projection of the top row (adjacent to skin) of the current probe location along with a history of the recorded images, also presented as coronal projections of the top row, on a profile-facing idealized torso.

B. Absolute and Relative Image Locations

Figure 12:
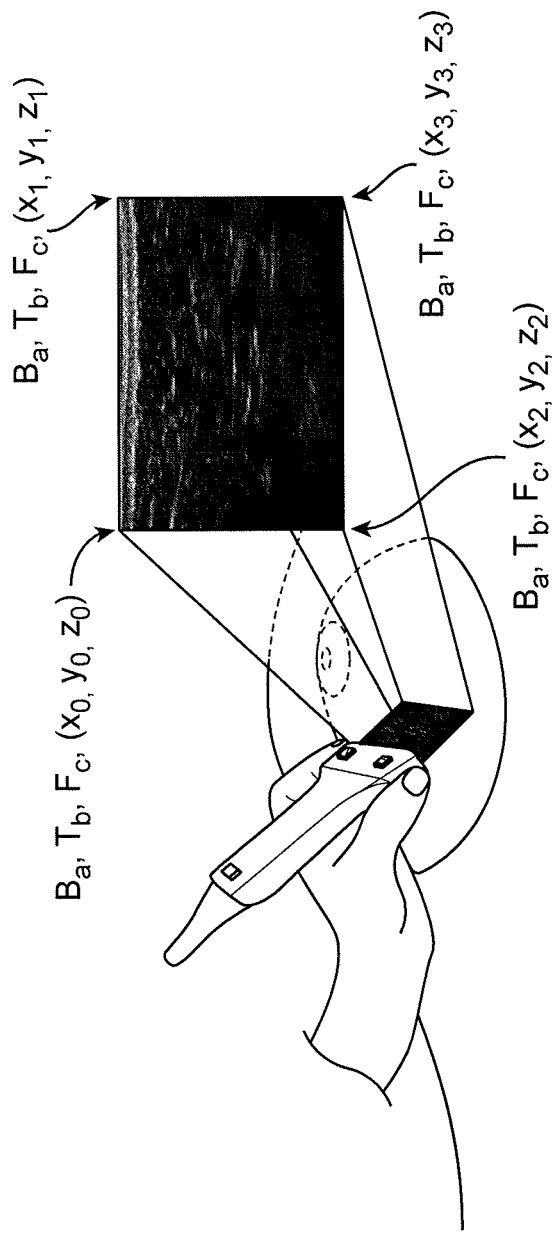
FIG. 12 illustrates position mapping of a scanned image in accordance with some embodiments.

In some embodiments, each image recorded by the tissue mapping system contemplated has location identifier information appended to the image file format (see FIG. 12). In further embodiments, those identification components are:

B, T, F (space holders for whatever identifier)
 i. $x_0$, $y_0$, $z_0$—the x, y, and z locations in space (relative to an arbitrary standard that is common to all images in that track) of the feature represented by the pixel in the upper left-hand corner of the image.
 ii. $x_1$, $y_1$, $z_1$—the x, y, and z locations in space (relative to an arbitrary standard that is common to all images in that track) of the feature represented by the pixel in the upper right-hand corner of the image.
 iii. $x_2$, $y_2$, $z_2$—the x, y, and z locations in space (relative to an arbitrary standard that is common to all images in that track) of the feature represented by the pixel in the lower left-hand corner of the image
 iv. $x_3$, $y_3$, $z_3$—the x, y, and z locations in space (relative to an arbitrary standard that is common to all images in that track) of the feature represented by the pixel in the lower right-hand corner of the image In some variations, the absolute accuracy of the locations of the position sensors, relative to the position transmitter is accurate to within 5 mm.

In other embodiments, the relative distances of the spacing of one recorded image to the subsequent recorded image within a single scan row, (i.e., the resolution of the image spacing within a single scan row) is accurate to within 1 mm.

In some embodiments, the relative distance between two, adjacent, images is measured by calculating the maximum of the distances between each of the four corners of the images ($\{x_0,y_0,z_0\}-\{x_1,y_1,z_1\}-\{x_1',y_1',z_1'\}$, $\{x_2,y_2,z_2\}-\{x_2',y_2',z_2'\}$, $\{x_3,y_3,z_3\}-\{x_3',y_3',z_3'\}$).

These distances may be found via the method of Pythagoras where:

$$\{x_0,y_0,z_0\}-\{x_0',y_0',z_0'\}=\text{sqrt}(\{x_0-x_0'\}^2+\{y_0-y_0'\}^2+\{z_0-z_0'\}^2)$$

Other methods and systems configured to determine the proper coverage and resolution of recorded images in a single or multiple scan rows are described in patent application Ser. No. 13/854,800 filed on Apr. 1, 2013; 61/753,832 filed Jan. 17, 2013; and 61/817,736 filed on Apr. 30, 2013, which are herein incorporated by reference in their entirety.

These location markers allow the user to identify the location of the image frame, therefore, a region of interest (ROI) in one frame relative to a landmark which was identified during the scanning process. In some variations, typical landmarks are the nipples (at the surface of the skin) in the Breast mode and the navel (at the surface of the skin) in the abdominal mode.

Because some tissue structures are more mobile than others, reference landmarks may move if the patient is repositioned between scan tracks. In order to accommodate the possibility that the reference may move if the patient is repositioned, some embodiments allow the user to establish a single reference mark for all of the recorded scan tracks, create a unique reference point for each scan track, or create a set of unique reference points, each point serving as a reference for a grouping of scan tracks.

In further variations, the images recorded by the tissue mapping system are intended for subsequent review, and not to guide an interventional procedure. The subsequent review may prompt a third, non-invasive, real-time, examination in which the ultrasound probe is placed in the general region of the ROI. As such, the absolute accuracy of the location of the ROI is within ½ of a probe width.

In some embodiments, the accuracy of the absolute location of any image recorded with the tissue mapping system described is intended to allow identification of a region of interest in a subsequent review and allow accurate placement of an ultrasound probe in a third, subsequent, diagnostic ultrasound procedure. As such, the system specifications are that the device will accurately locate that region of interest, thus the absolute location of the probe, within one-half of the width of the ultrasound probe. This accuracy may not be sufficient to determine the appropriate placement of a needle (for biopsy) or tissue marker, or to direct other interventional procedures without real-time imaging.

In other variations, if the patient or tissue structure moves more than ½ of a probe width between the recording of a scan track, the user should re-define reference marker before recording the next scan track. If the patient or tissue structure moves more than ½ of a probe width during the recording of a scan track, it is the user's responsibility to re-define reference marker and re-record that scan track..

C. Locating the Reference Point and Vector

Figure 13:
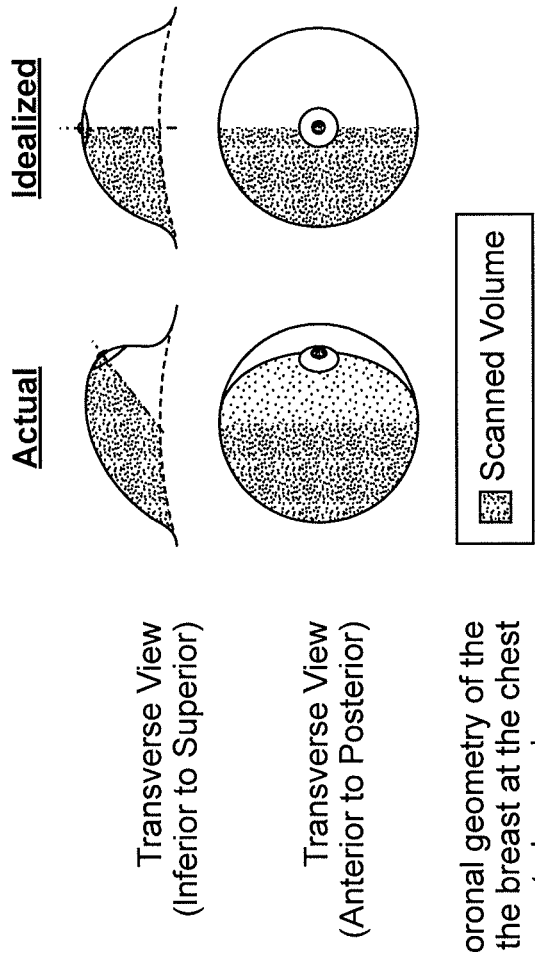
FIG. 13 illustrates compensating for actual versus idealized tissue geometries in accordance with some embodiments.

In some embodiments, one or more scan tracks are referenced to the projection of an anatomic structure on the coronal plane. In some variations, each scan track recorded is referenced. For example, in the case of the breast exam that reference maker is assumed to be the nipple—as that nipple would be located in an idealized breast geometry. Referring to FIG. 13, if "half" of the breast is scanned on one side of a plane transecting the nipple and the midline of the breast, then that scan will cover half of the tissue of the breast, regardless of the actual geometric orientation of the breast. In other words, the recorded images on one side of the reference point are mapped to be on the same side of the idealized tissue image.

1. Marking the Reference

Figure 14:
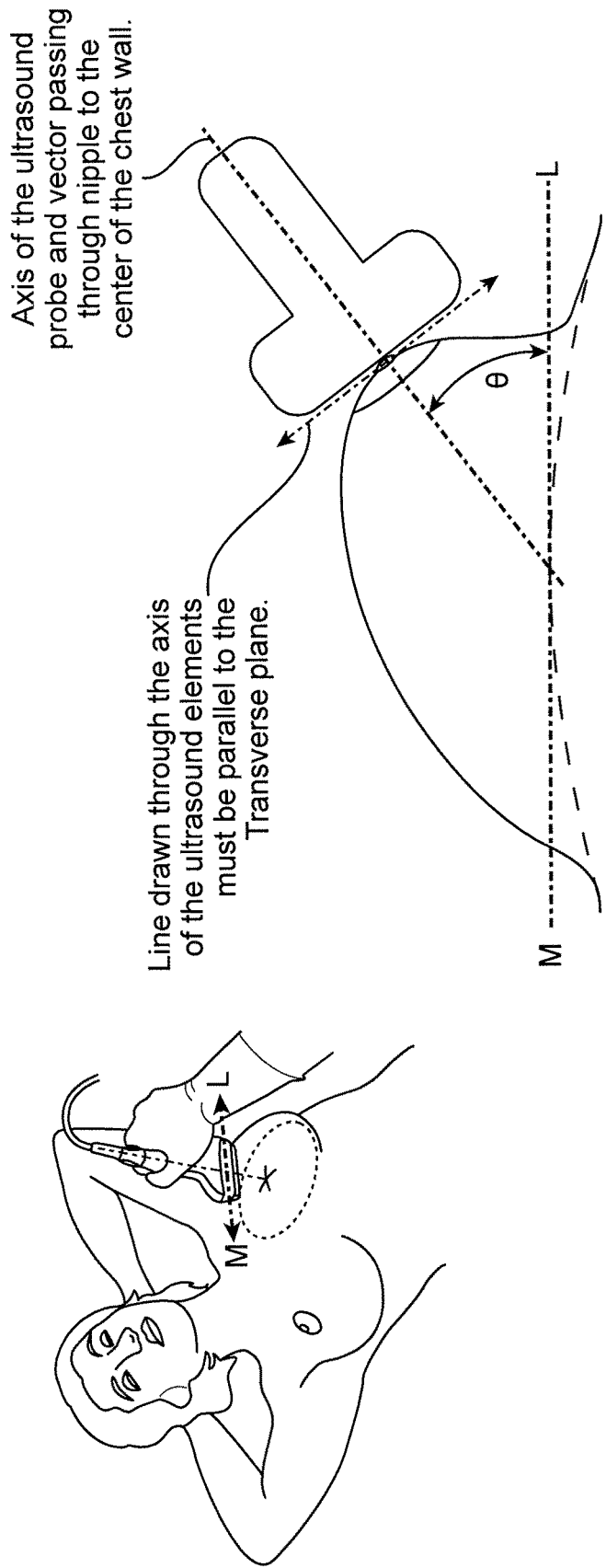
FIG. 14 illustrates the alignment of an ultrasound probe relative to a body in accordance with an embodiment.
Figure 15:
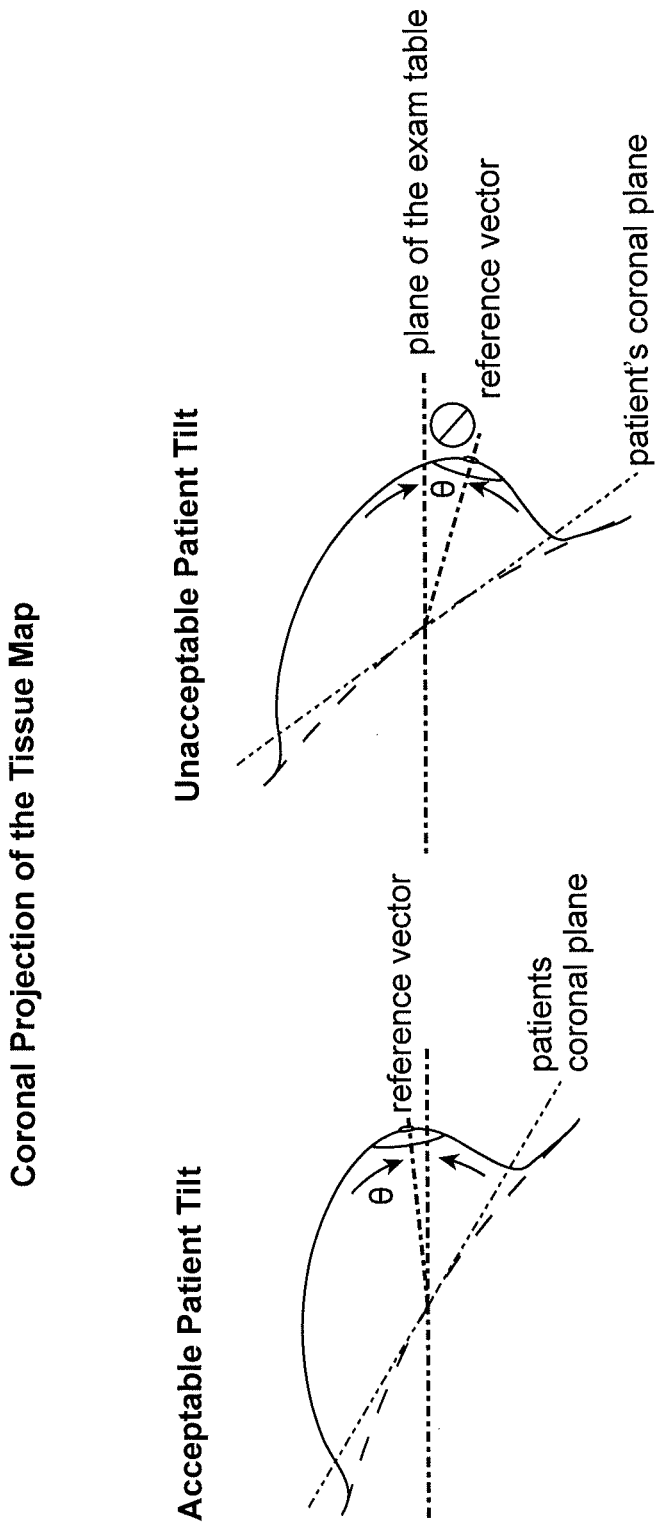
FIG. 15 illustrates a coronal projection of the tissue map in accordance with some embodiments.

In some embodiments, to mark the reference the imaging device such as an ultrasound probe should be placed on the reference point to establish an axis or plane. For ultrasound breast imaging, an ultrasound probe is placed on the nipple such that the center of the row of imaging elements is on the nipple and the line represented by the row of imaging elements is parallel to the Transverse plane (that is, a projection of that line on the coronal plane will be in the medial-lateral direction). As shown in FIG. 14, the probe handle should be angled toward the center of the breast on the chest wall. Thus, the vector passing through the middle of the handle and through the middle of the imaging elements should also pass through the nipple and the middle of the breast on the chest wall.

a. Rotating the Patient (See FIG. 15)

The reference may be marked, even if the patient is rotated to allow better access to portions of her anatomy. If the angle between the nipple/center-of-the-breast vector and a horizontal plane (such as one that is parallel to the surface of the exam table) is less than 0, however, the system may not be able to calculate a reference point.

2. Coverage and Sections

Figure 16:
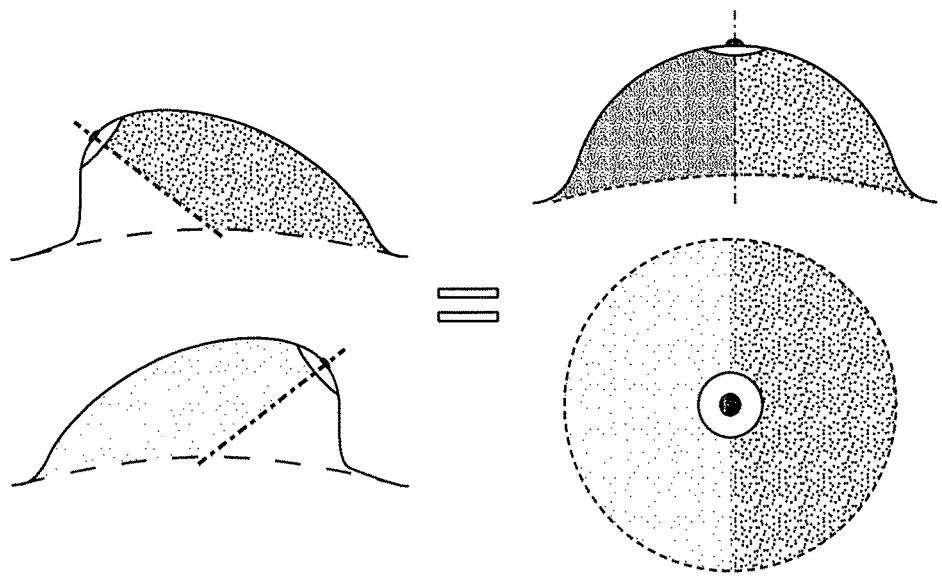
FIG. 16 illustrates an example of reconstructing coverage sections on an idealized structure to determine the coverage of the scan.

In some cases, by marking a new reference point when the patient or the tissue structure is moved, the user may map the entirety of the structure with complete coverage. For example, marking the reference point and scanning half of the breast when it is located in one position, and scanning the other half when the breast is located at another position—if the new reference point is identified first, results in complete coverage of the breast structure. (See FIG. 16)

Figure 17:
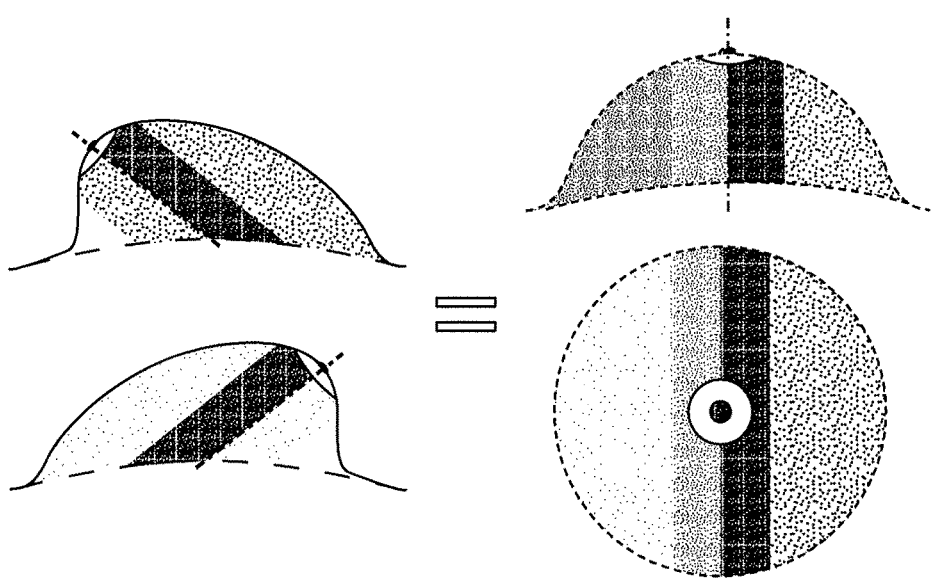
FIG. 17 illustrates an example of overlapping scan images in accordance with some embodiments.

In order to improve the quality of coverage, overlapping sections of the tissue may be scanned. FIG. 17 shows scanning at the intersecting section boundaries.

D. Scaling the Recorded Images

The idealized vs actual tissue geometry is described in the first section. The breast size and separation of the breasts can vary from woman to woman (see FIG. 18). In some embodiments, the tissue mapping system takes the recorded images, and associated locations, and displays them on an idealized breast profile. In order to accomplish this task it may be desirably to normalize actual locations and project them on to the idealized geometry.

Figure 19:
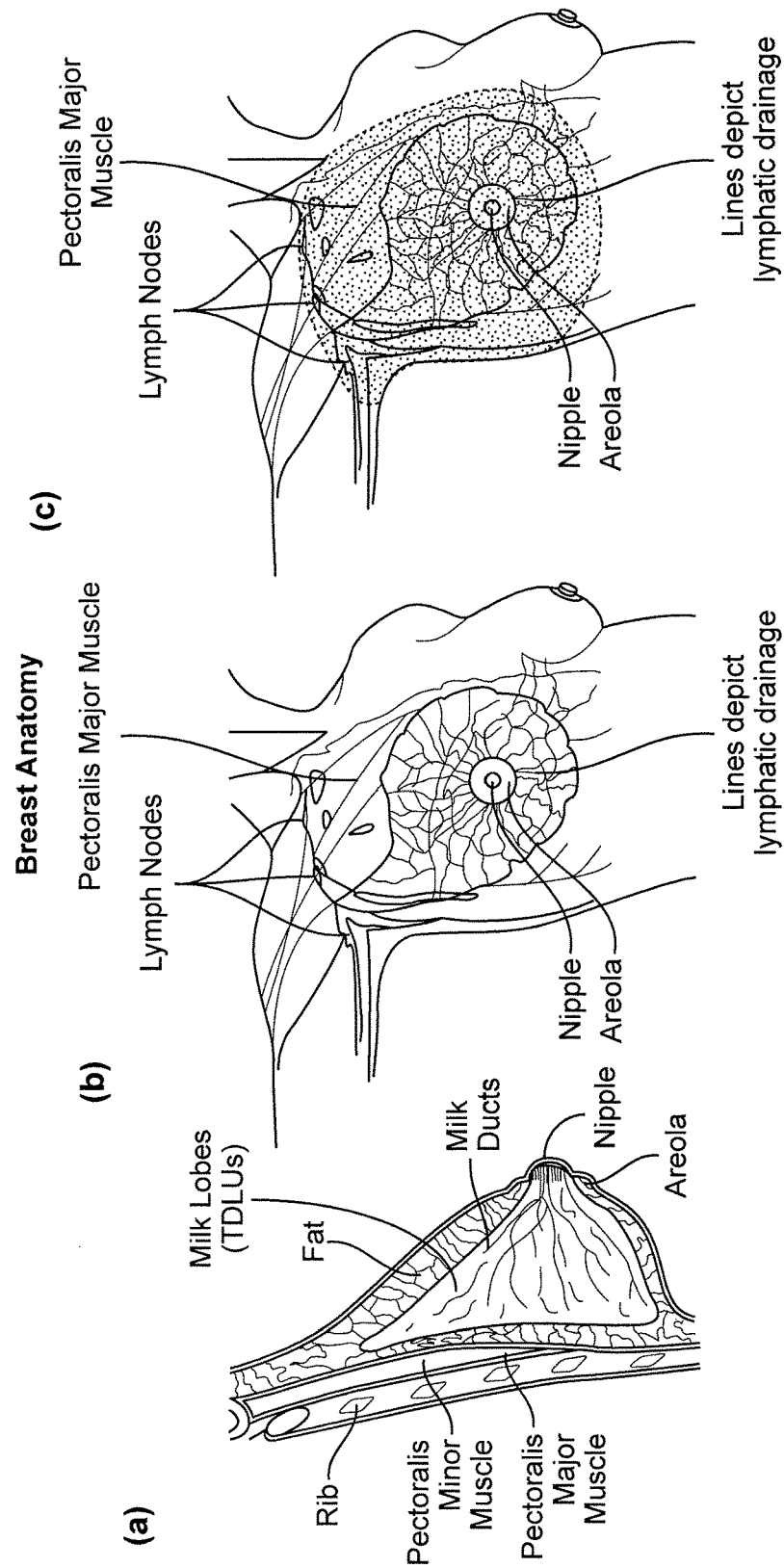
FIGS. 19A-19C illustrate various views of the breast anatomy.

The breast tissue is not confined to the pendulous structure that protrudes from the chest wall (FIG. 19A). It is located from just lateral of the sternum to under the arm pit (the axillary tail) (FIG. 19B). Because breast imagers are concerned with reviewing the lymph nodes that drain the breast, in addition to the actual breast tissue, it may be desirable to image the entire area from the clavicle to the bottom of the rib cage, and from the sternum to the axilla under the armpit (FIG. 19C).

In order to scale within these medial boundaries the "center" of the breast can first be established. As described above, the breast is mobile and the actual orientation may vary from the ideal orientation (i.e., where the nipple protrudes directly anterior to the center of the breast at the chest wall and the coronal plane of the breast (that is, the plane which is orthogonal to vector running from the nipple to the middle of the breast at the chest wall) matches the coronal plane of the chest.)

Identifying this "center" is described above, and will provide the location of the nipple and the location of the center of the breast at the chest wall. This process will also establish the medial-lateral vector as well as the "coronal" plane of the breast.

After the "center" of the breast is identified, it may be desirable to identify the medial and lateral-boundaries, the superior-inferior boundaries, and the actual sagittal and coronal planes. A scan row from along the sternum, from the clavicle to the bottom of the rib cage will establish the medial boundary, as well as the superior-inferior boundaries and the coronal plane. A scan along the axilla will establish the lateral boundaries, as well as the sagittal plane and reconfirm the inferior boundary. (See FIG. 20).

It is not necessary to rely on one set of reference coordinates for the entire breast. As will be described in the following section, when the breast mobilizes and the reference geometry of the breast changes from the reference geometry of the patient's body, it reference coordinates can be reestablished for subsequent scan information.

It may be possible to obtain the superior boundary and/or the medial boundary, and/or the lateral boundary and/or the patient's coronal plane by scanning a medial-lateral path adjacent to, and parallel with, the patient's sternum. (See FIG. 21)

E. Reconstructing the Images to Reflect Ideal Breast Map

Once the relative coronal plane of the breast, the nipple-to-middle-of-chest-wall vector, the medial and lateral boundaries, the superior and inferior boundaries, the patient's sagittal plane, the patient's coronal plane, and the patient's medial-lateral alignment have been identified, the recorded images may be reconstructed for viewing on a breast or tissue map.

The idealized vs actual tissue geometry is described in the first section. The breast may be scanned at different orientations and it is desirable to normalize idealized locations from actual locations based on the relative locations of landmarks, such as the nipple.

Figure 22:
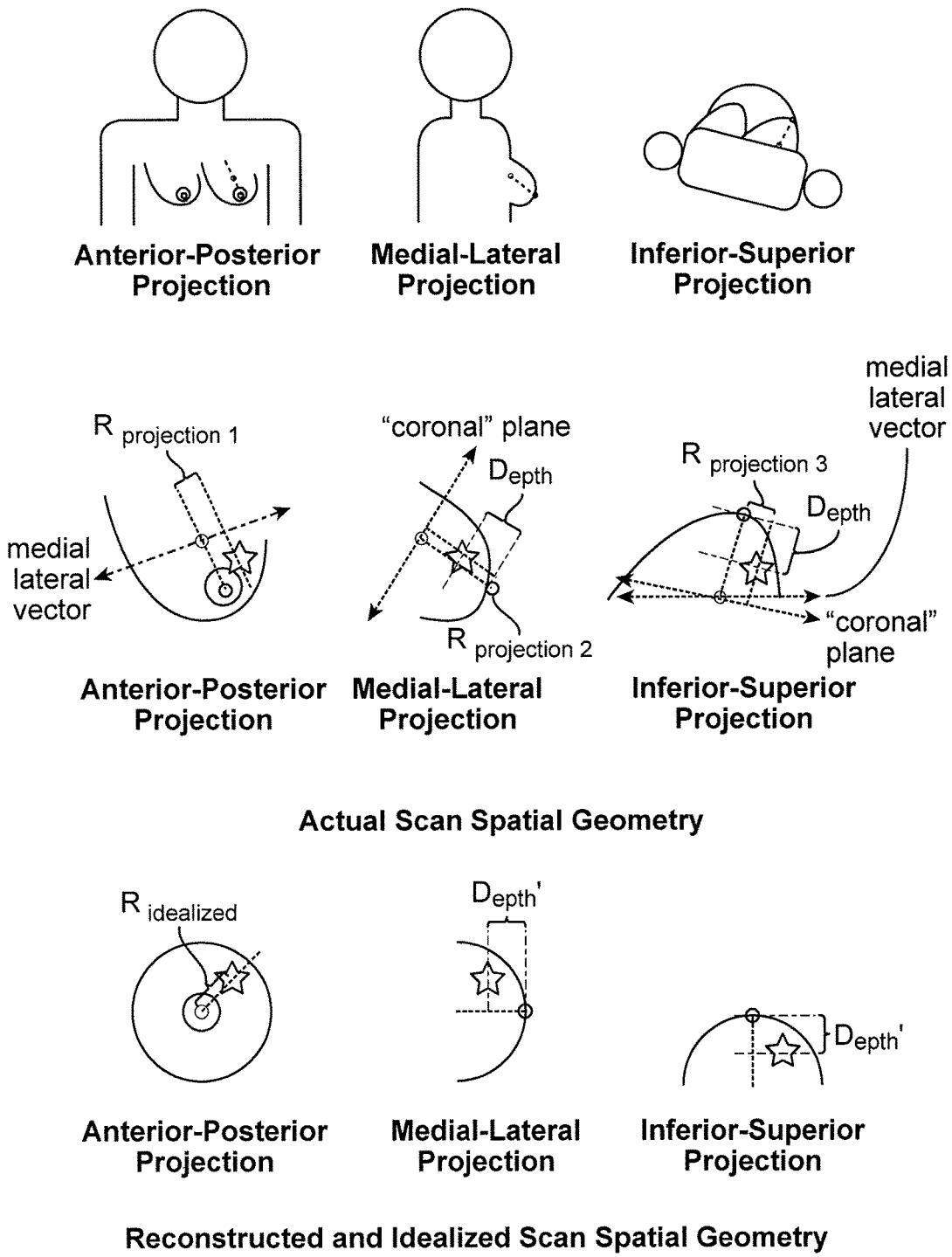
FIG. 22 illustrates various views of a lesion mapped on the actual scan spatial geometry and idealized scan spatial geometry when the patient is on their side in accordance with some embodiments.

The idealized location may be constructed from the nipple-to-center-of-breast vector, the medial-lateral vector, and the projected coronal plane (found during the reference mark). (See FIG. 22)

In some embodiments, after the reference locations have been identified then all scan locations are adjusted from those reference marks until the patient moves.

1. Correcting the Relative Orientation of the Features:

In some embodiments, the system measures the locations relative to the nipple-to-middle-of-chest-wall vector. Since that vector is orthogonal to the coronal plane, the relative coronal plane is identified. Since the actual coronal plane (medial scan) and sagittal plane (lateral scan) are known, the orientation of features may be reconstructed by several methods, including:

i. Trigonometric Reconstruction

Rotating all of the features along the pivot of the intersection of the nipple-to-chest-wall vector and the coronal plane of the breast until the coronal plane of the breast matches the coronal plane of the patient and the nipple-to-middle-of-chest-wall vector protrudes directly anterior to the chest wall, and ii. Geometric Reconstruction (Pythagorean)

Determining the distance of the features from the reference points using the method of Pythagoras (taking the square root of the sum of the squares of the distances of the x, y, and z locations of the features from the x', y', and z' locations of the references and transforming those distances to new locations (x", y", and z") relative to the standard reference of the idealized breast ($x_0$, $y_0$, and $z_0$).

2. Adjusting the "Height" of the Breast:

Adjusting the "Height" of the features as a function of the ratio to the length of the nipple-to-middle-of-chest-wall vector and the height of the idealized breast on Breast Map.

3. Adjusting the "Size" of the Breast:

The width and height of the features may be adjusted to scale to the distance between the medial scan and the lateral scan and the features may be overlain on the idealized breast map.

4. Multiple Scans and Multiple Reference Points

In some embodiments, it is not necessary to use the same set of reference coordinates for the entire breast scan. There may be incidences where the patient may be lying on her side while part of the breast is scanned, and lie on her back while another part is scanned. (see FIG. 23)

Although the actual spatial location of the reference coordinates, that is the patient's coronal and sagittal planes, medial-lateral vector, and the center of the breast at the chest wall, will not change relative to the patient's actual body. The relative position of the nipple to those structures, and the shape of the breast, may change, however.

Figure 20:
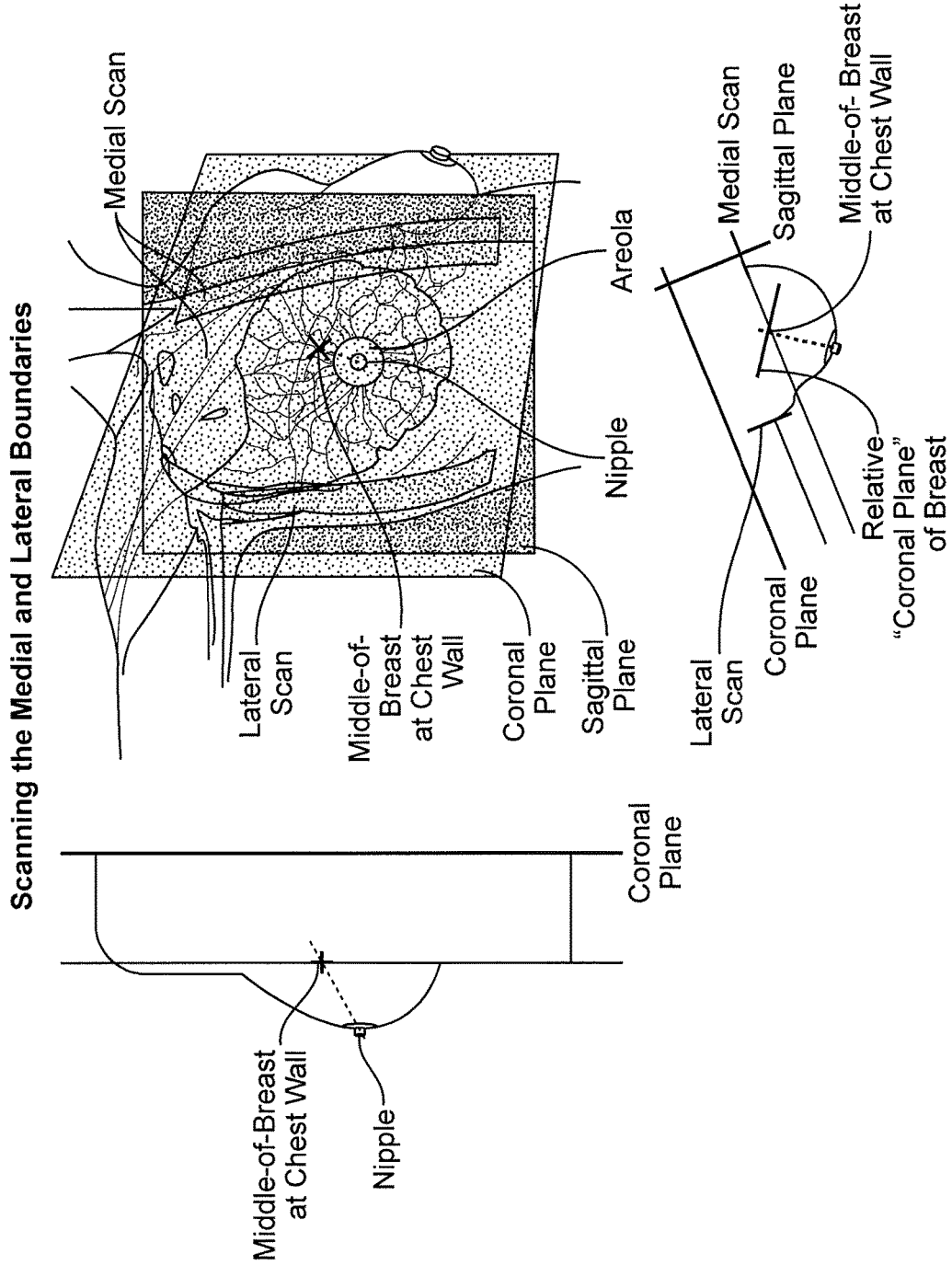
FIG. 20 illustrates various views and planes of the breast anatomy scanning the medial and lateral boundaries in accordance with some embodiments.
Figure 21:
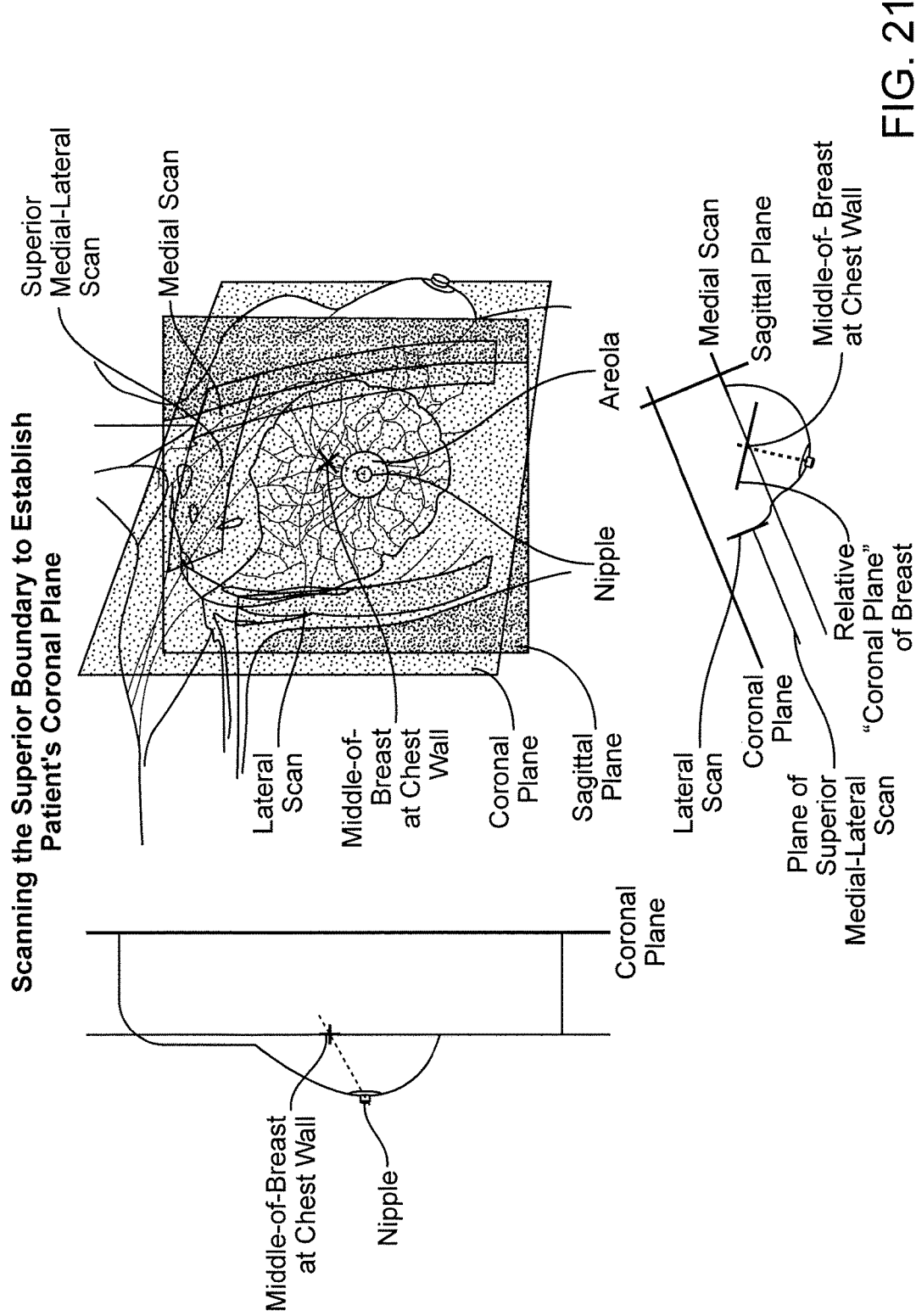
FIG. 21 illustrates various views and planes of the breast anatomy scanning the superior boundary to establish the coronal plane in accordance with some embodiments.

Since the normalization process reduces all of the information that are obtained from scans that are performed to an idealized breast geometry, that normalization process also allows different sets of information, obtained when scanned to different sets of reference information, to be overlain on the ideal breast geometry (see FIGS. 20 and 21).

Figure 24:
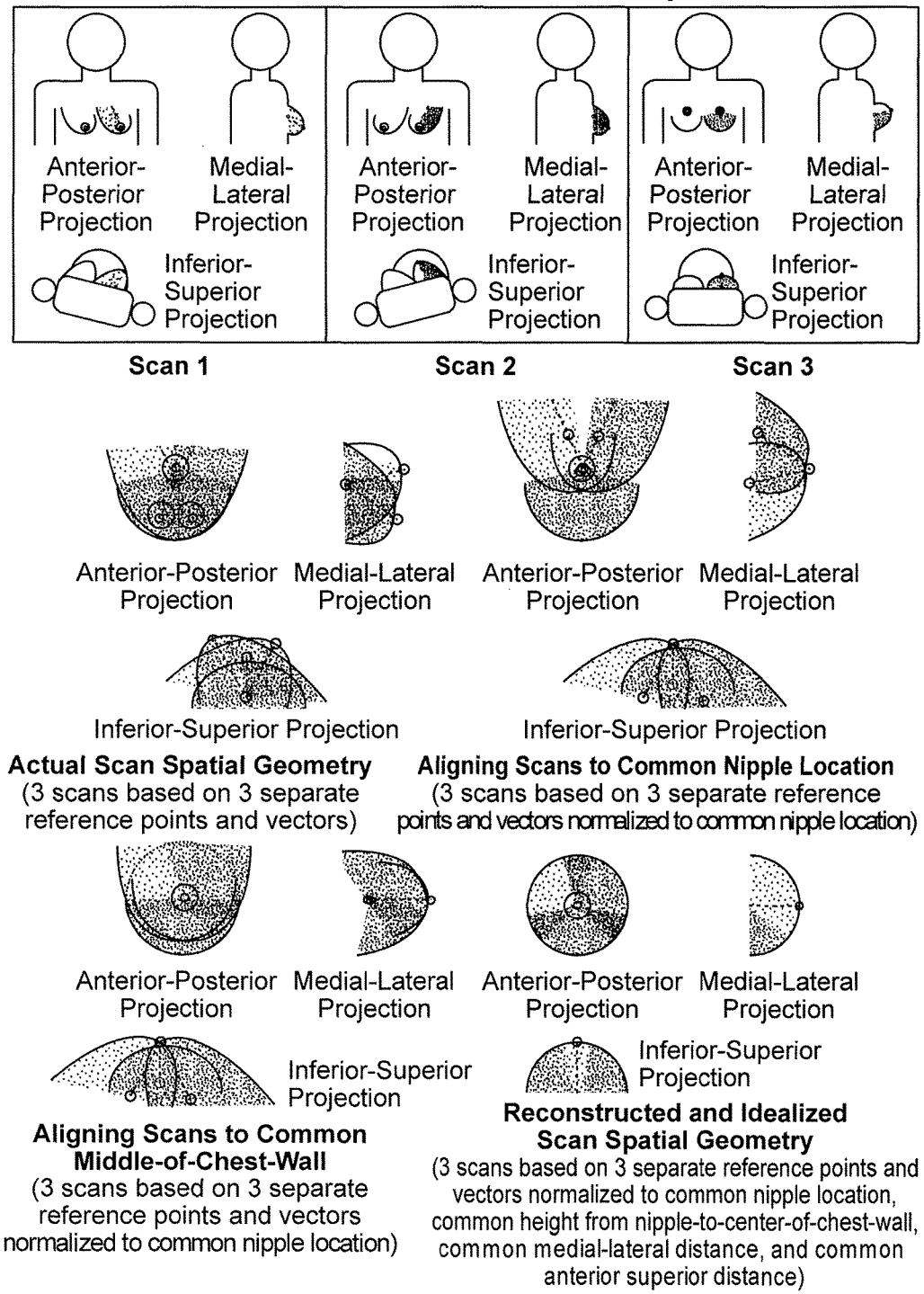
FIG. 24 illustrates various views of scan sections mapped on the actual scan spatial geometry and idealized scan spatial geometry when the patient is in various positions in accordance with some embodiments.

In some embodiments, these geometries are normalized by (see FIG. 24):

i. Aligning the nipple locations for each section to a common spatial location, ii. Aligning the nipple-to-center-of-chest-wall vector to a common direction for all sections, iii. Adjusting the nipple-to-center-of-chest-wall height to a common distance—and adjusting the "height" of surrounding structures, of each section to match a common structure, and iv. Adjusting the medial-lateral and superior inferior scaling for all structures in each section to match.

5. Absolute Accuracy in Reconstructed Breast Profiles

It is important to note that, in the case of a screening ultrasound procedure, the mapped information may be used to guide a second, non-invasive, diagnostic ultrasound procedure. In some embodiments, the information will not be used to guide an interventional procedure involving scalpels, needles, or radiation.

For instance, if the scanner is scanning the breast from the inferior to the superior direction, some tissue may compress in front of the probe, similar to the snow plow on a train. The tissue containing the lesion may be pushed somewhat superior before the probe reaches the point where that lesion may be imaged (see FIG. 23).

Figure 25:
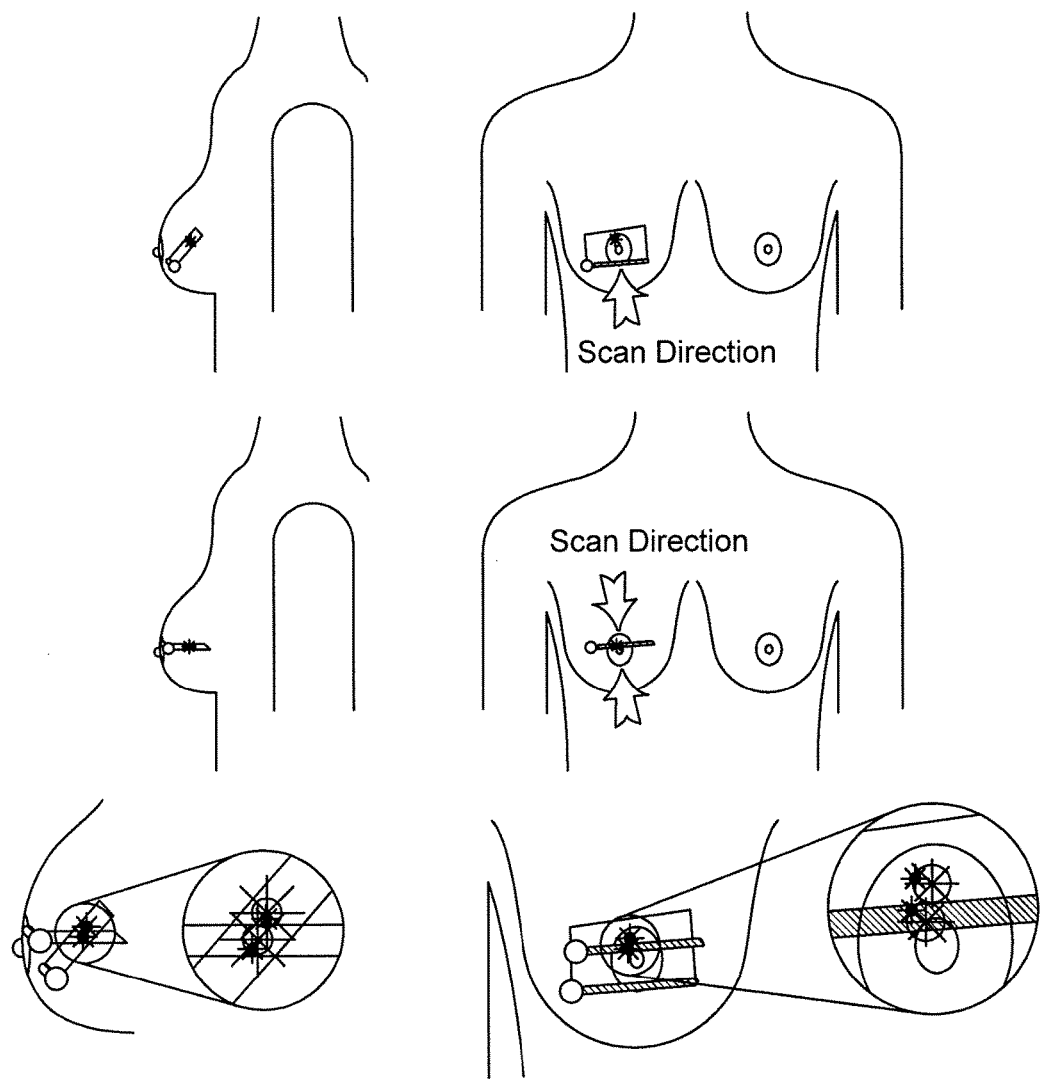
FIGS. 25-26 illustrate variances in mapping the tissue due to the scan pattern or differences in the reference geometry.

The opposite might be true if the breast were scanned from the superior to the inferior direction. The tissue containing the lesion might be pushed inferior before it is imaged. FIG. 25 shows variances in absolute mapping of the same area due to differences in scan patterns or reference geometries. In some variations, the transformation from actual to ideal breast geometry may result in slight offsets when a feature is imaged using one set of calibration factors as opposed to another.

The follow-up examination post ultrasound screening involves diagnostic ultrasound. In the diagnostic ultrasound procedure it is desirable that, when the sonographer places the probe at the location of the "mapped" lesion that the "mapped" lesion appear.

Since the calibration parameters for the "mapped" lesion location may not match the patient orientation at the time of the diagnostic exam (for example, the breast may be mobilized differently from body so that the angle and length of the nipple-to-center-of-breast vector is different) the sonographer may have to rotate the probe, once placed on the lesion "location" to actually find the lesion.

Figure 26:
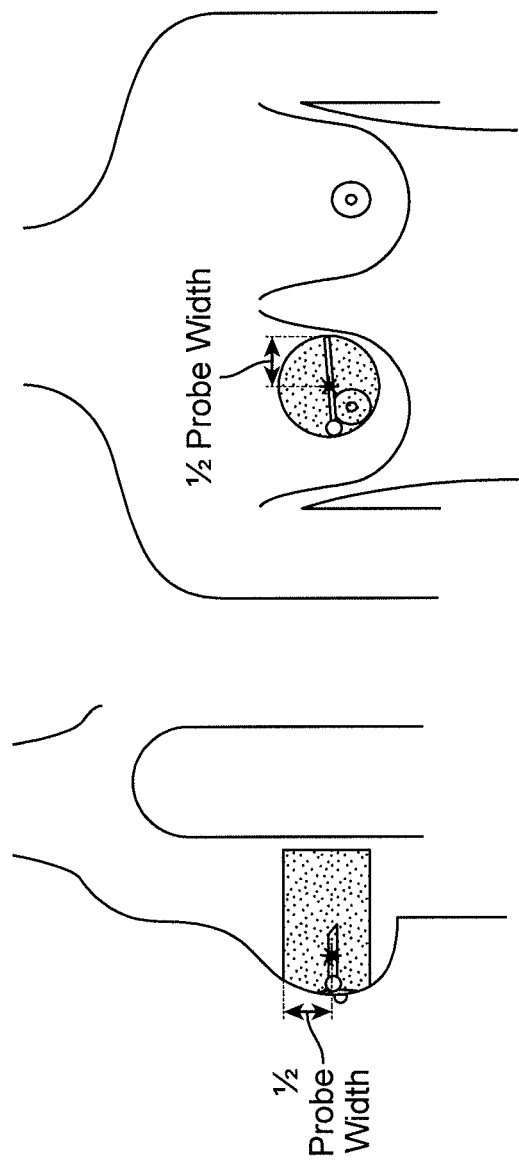

In some embodiments, the "mapped" location may only be accurate to within ½ of a probe width. (See FIG. 26)

F. Logical Description of the Location and Scaling Process

Once the relative coronal plane of the breast, the nipple-to-middle-of-chest-wall vector, the medial and lateral boundaries, the superior and inferior boundaries, the patient's sagittal plane, the patient's coronal plane, and the patient's medial-lateral alignment have been identified, the recorded images may be reconstructed for viewing on a tissue or breast map.

The idealized vs actual tissue geometry is described above. The breast may be scanned at different orientations and the system may normalize idealized locations from actual locations based on the scan parameters obtained at the beginning of the procedure.

Figure 27:
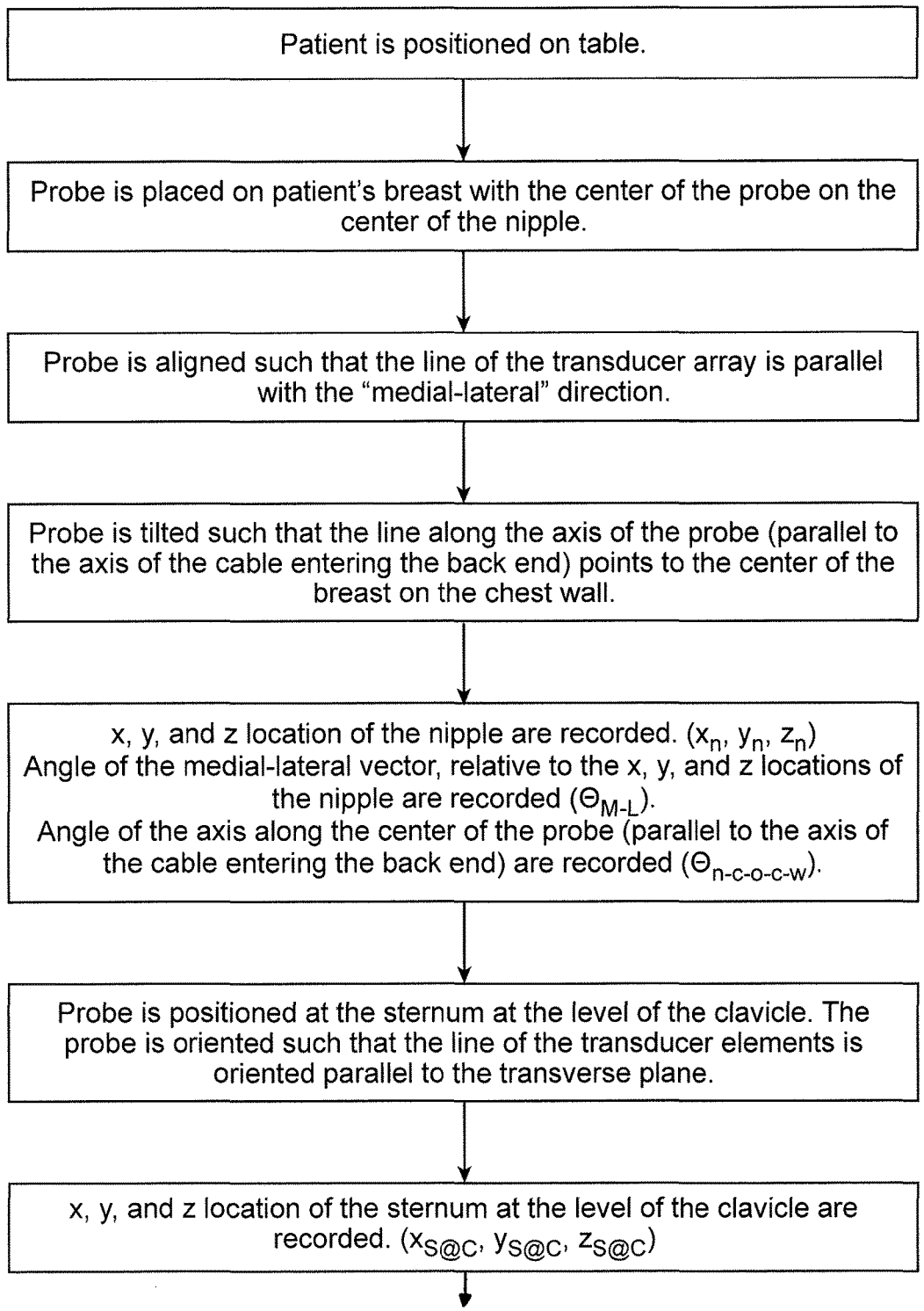
FIGS. 27-30 are flow charts illustrating scanning sequences in accordance with some embodiments.
Figure 28:
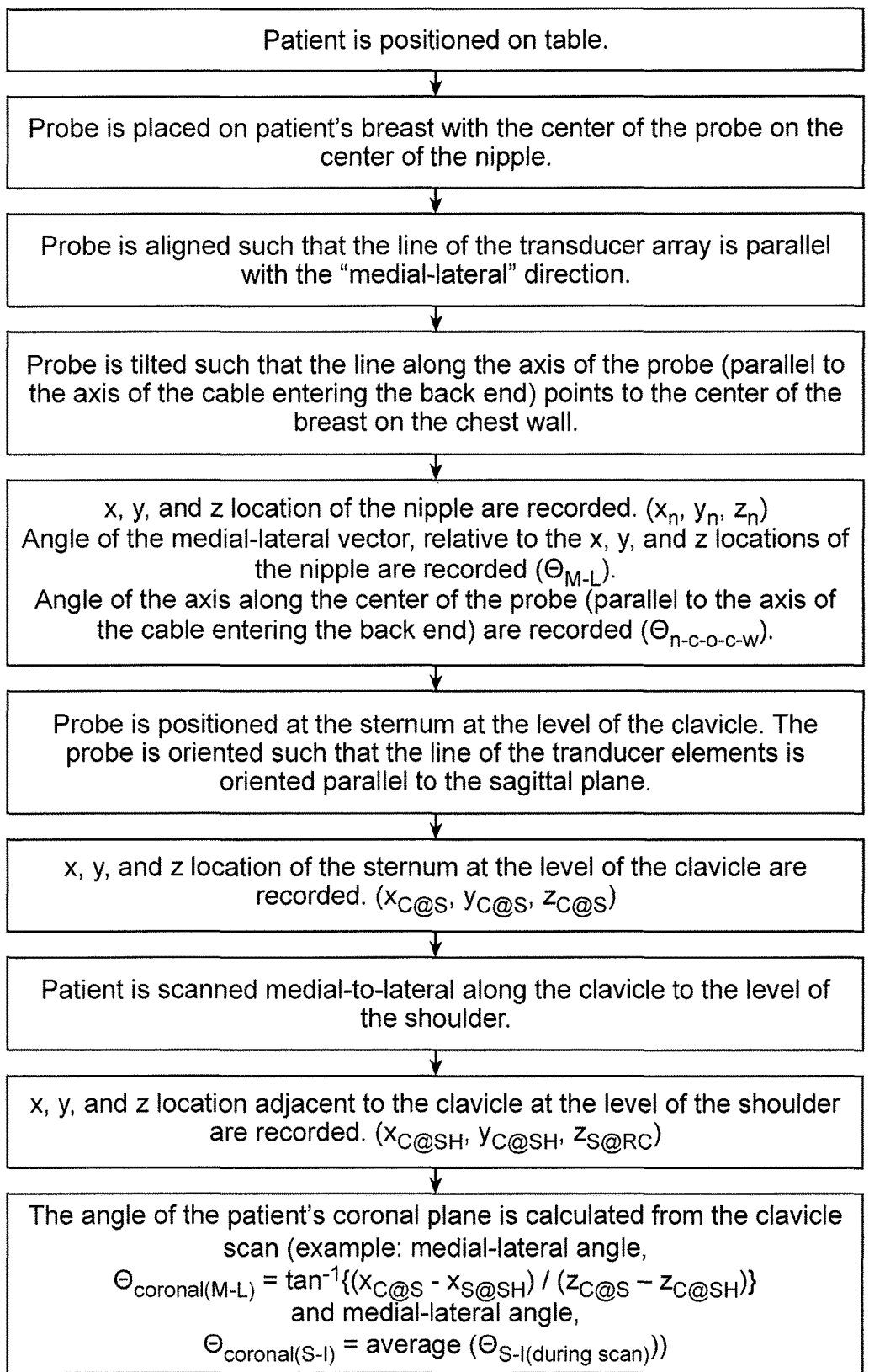

In the case of a breast scan, if the scan parameters are obtained by a vertical scan along the sternum and an orthogonal vertical scan along the side, starting under the rib cage, an example method in accordance with some embodiments is illustrated in FIG. 27. If the scan parameters are obtained by a horizontal scan along with and parallel to the clavicle, an example method in accordance with some embodiments is illustrated in FIG. 28.

G. Patient Positioning

Figure 32:
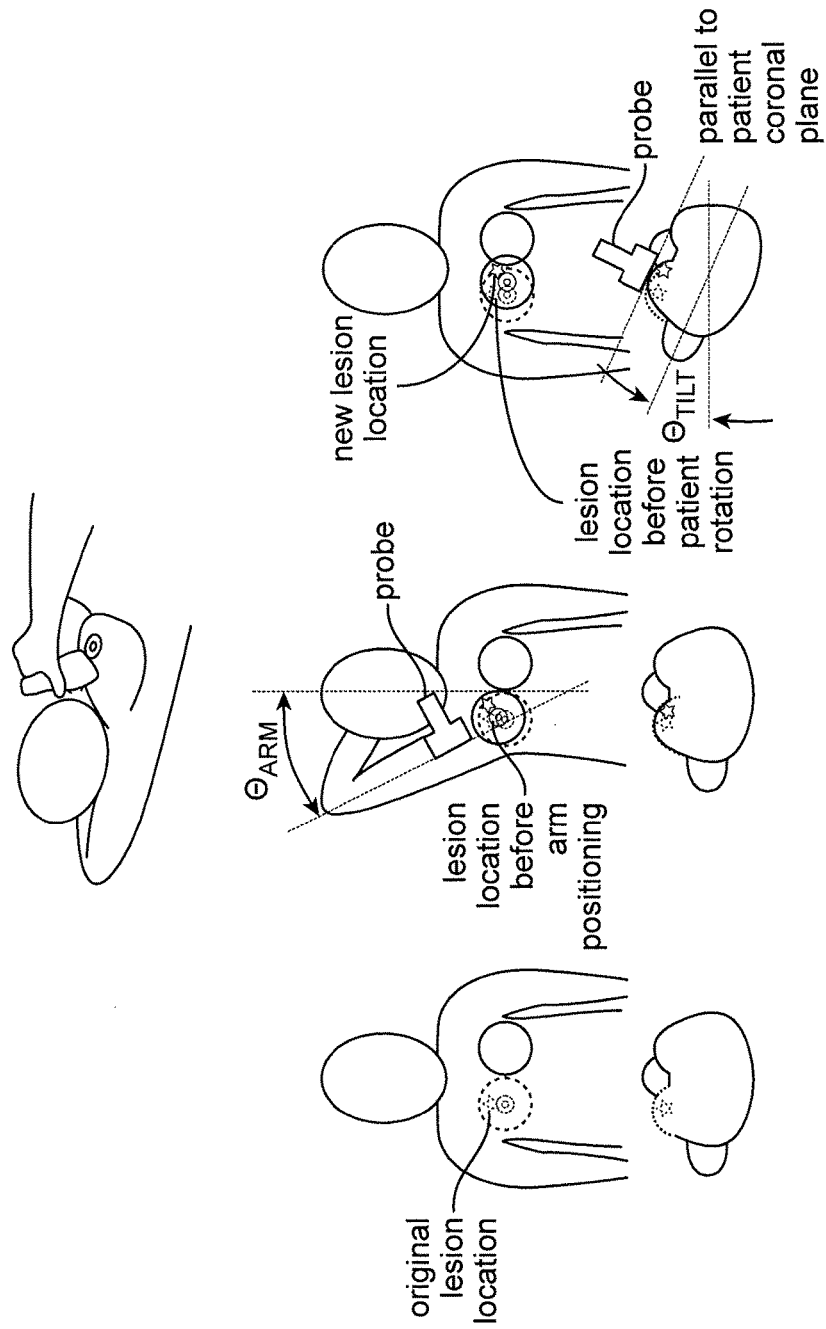
FIG. 32 illustrate a lesion on a breast of a human body relative to the body in different positions in accordance with some embodiments.

Since the breast tissue is mobile, it can sometimes be desirable to replicate the breast orientation and the subcutaneous structures of the patient's breast. (See FIG. 32) For instance, if the patient is lying on her back, with her arms to her side, the breast will be oriented in one manner and any lesion in that breast will have a relative orientation (with regard to the nipple). If the patient raises her arm, the breast will mobilize and, perhaps rotate underneath the skin. That lesion that was located at one position relative to the breast when the patient was lying on her back (with her arms to her side) might move, or rotate, as well. If the patient is rotated the breast will also mobilize and move relative to the nipple. That lesion that was located at one position relative to the breast when the patient was lying on her back (with her arms to her side) might move as well.

In some embodiments, during a diagnostic follow-up examination it is sometimes desirable for the utlrasonographer to replicate the original patient positioning so that the subsequent examination can locate the lesion at, relatively, the same location (relative to the nipple) as it was during the original examination. It is possible for the position to be replicated if the important patient positioning factors, such as patient rotation or arm position can be recorded for replication.

In some embodiments, these positioning factors can be determined because:

a. The plane of the floor is known because the sensor receiver is on the floor. The patient's coronal plane is known because it is determined during the positioning calibration. Therefore, the patient rotation (the angular difference between the plane of the floor and the patient's coronal plane) can be determined.

b. The transverse plane is known because it is orthogonal to both the patient's coronal plane and the patient's medial-lateral vector, both determined during the positioning calibration. If the probe is placed on the arm such that the line described by the ultrasound elements is parallel to the line described by the axis of the humerus, then the angular deviation of the arm to the transverse plan can be determined.

H. Logical Description of Patient Positioning Measurement

Once the relative coronal plane of the breast, the nipple-to-middle-of-chest-wall vector, the medial and lateral boundaries, the superior and inferior boundaries, the patient's sagittal plane, the patient's coronal plane, and the patient's medial-lateral alignment have been identified, the patient positioning may be reconstructed.

Figure 29:
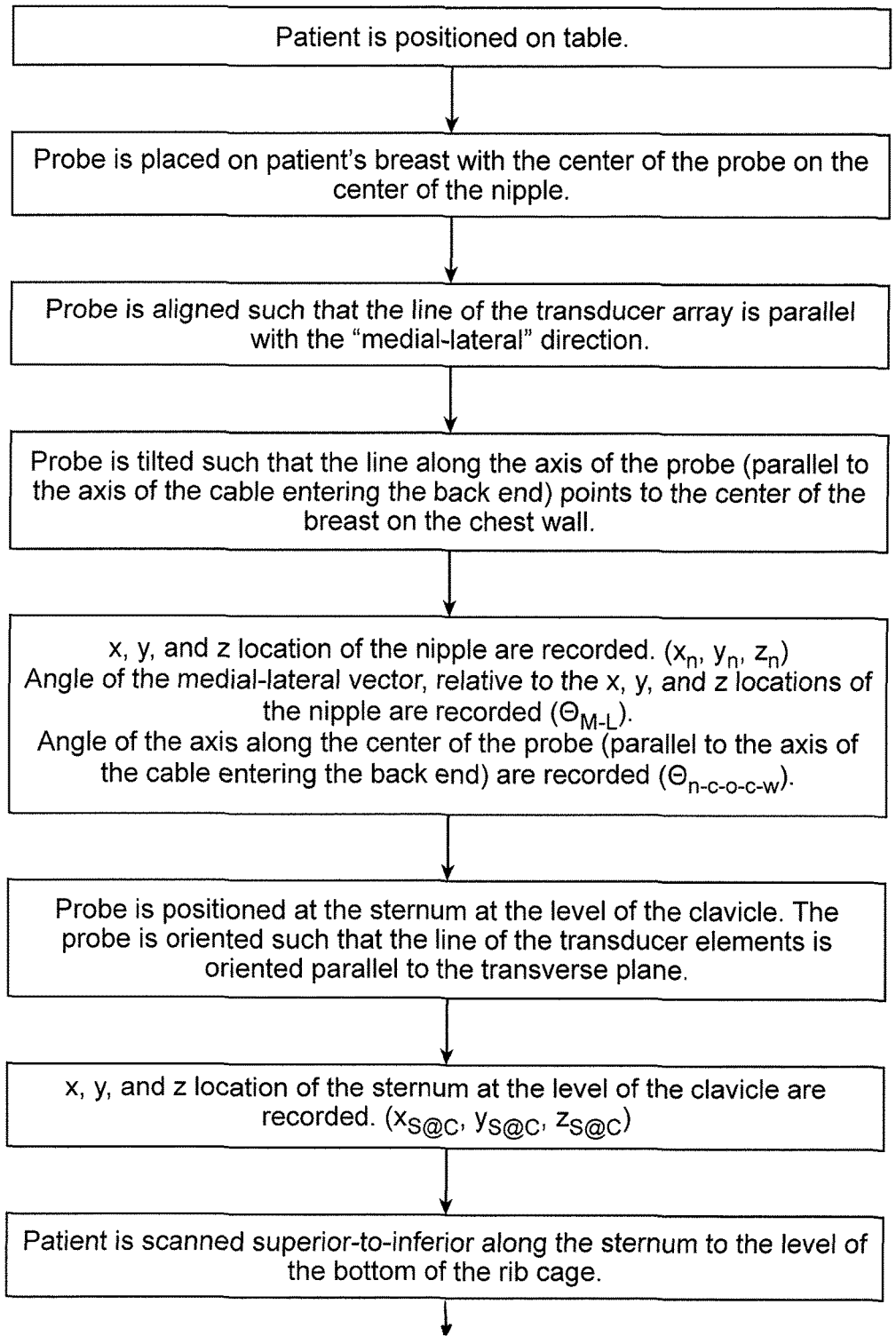
Figure 29:
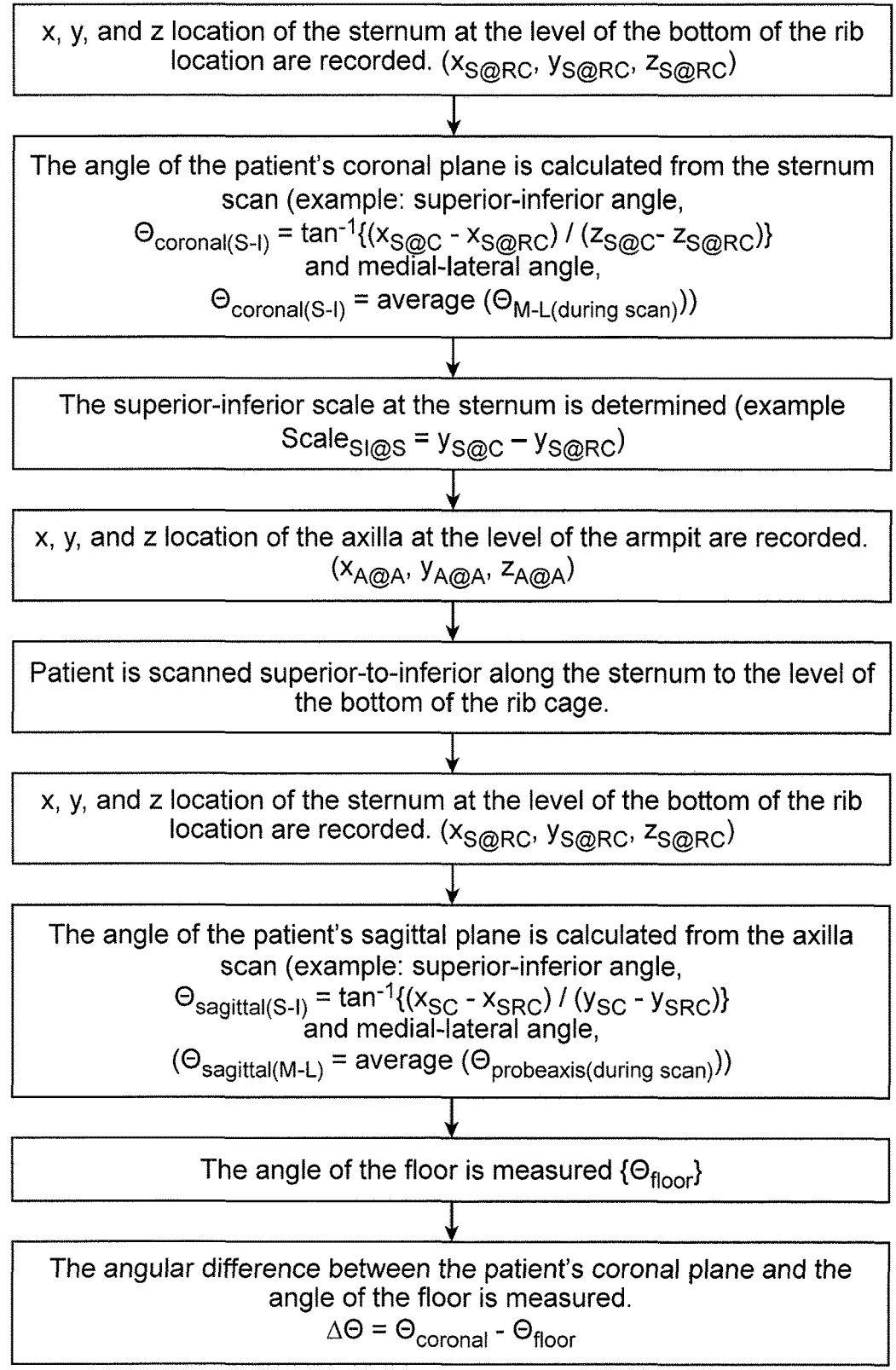

In some embodiments the patient rotation may be determined as illustrated in FIG. 29.

Figure 30:
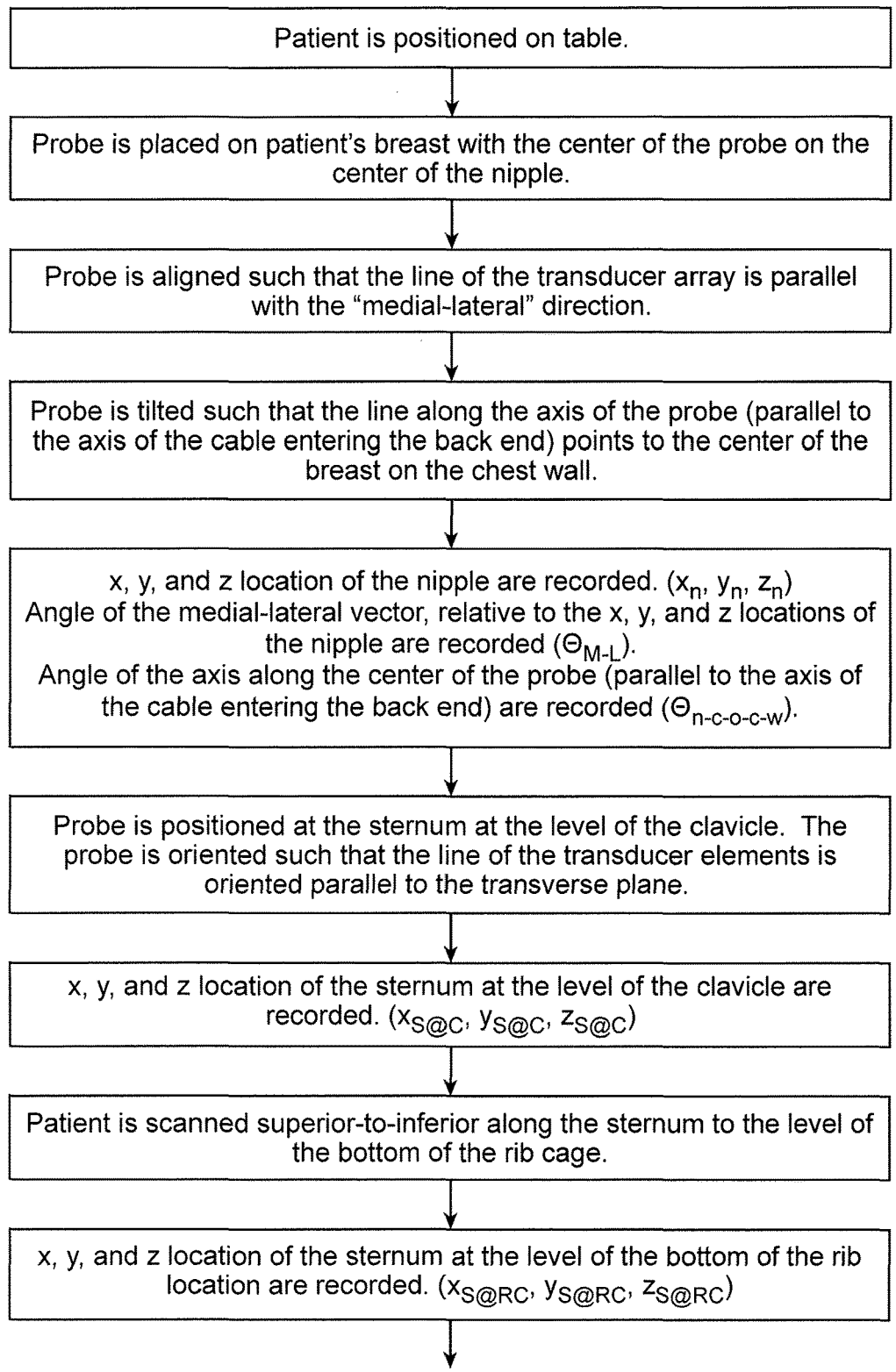
Figure 30:
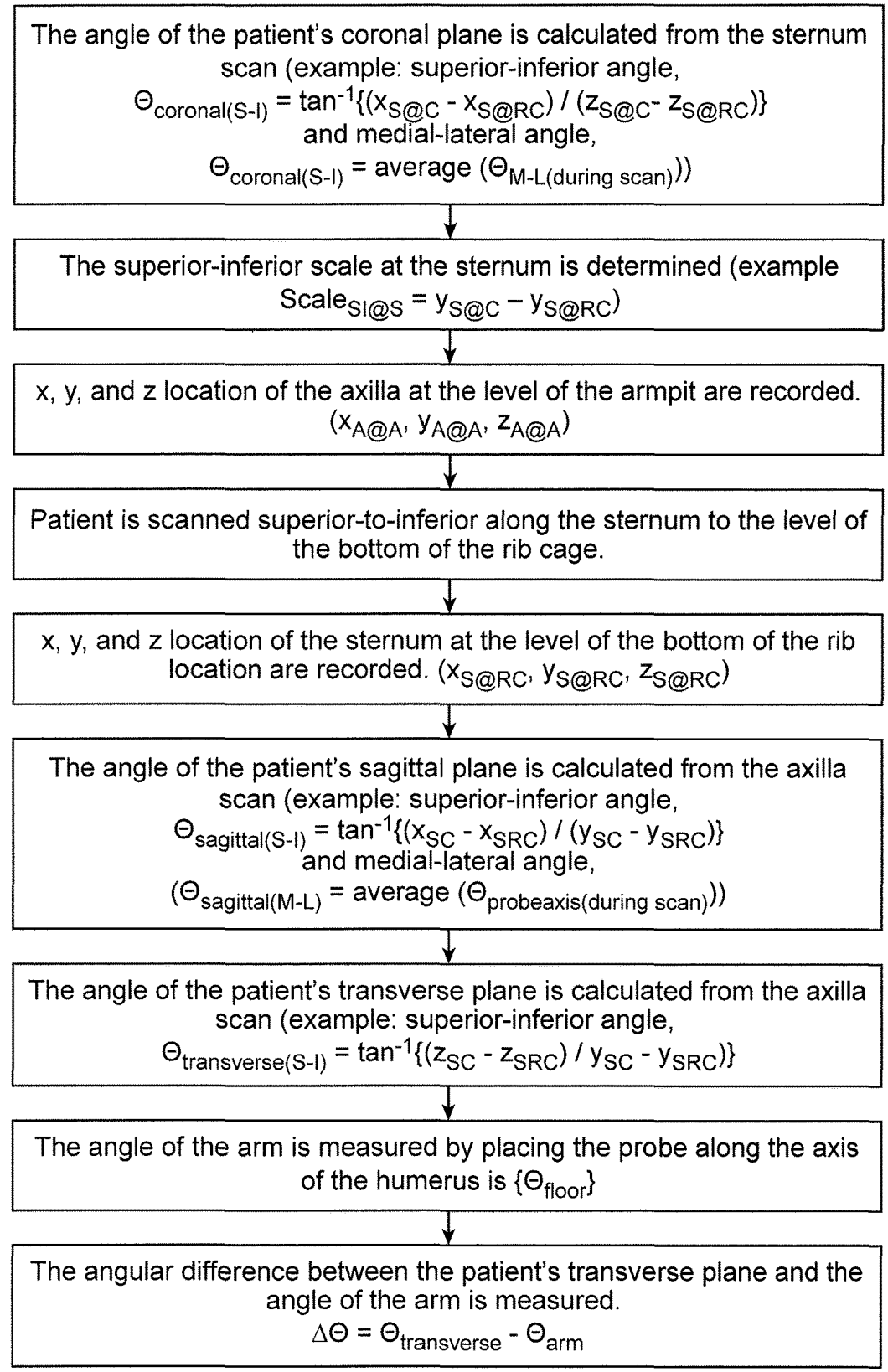

In some embodiments the arm position may be determined as illustrated in FIG. 30.

I. Systems for Tissue Mapping

Figure 31:
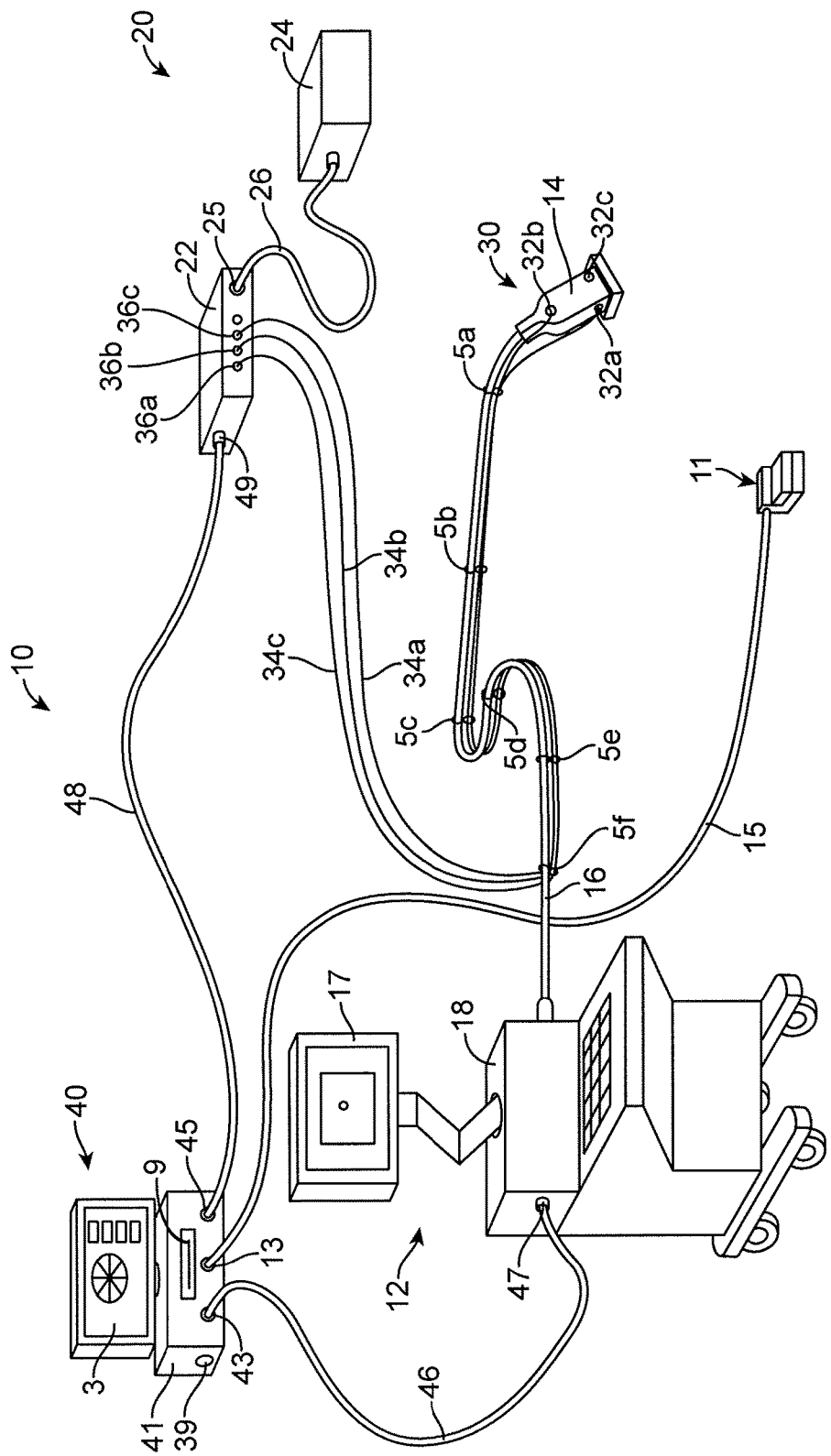
FIG. 31 illustrates aspects of a tissue scanning and imaging system in accordance with embodiments disclosed herein.

Referring to FIG. 31, two principal subsystems are illustrated. A first subsystem is the hand-held imaging system 12, which includes hand-held imaging monitor console 18, display 17, hand-held imaging probe 14 and connecting cable 16. A second system (referred to hereinafter as the "Image Recording and Tissue Mapping System"), according to the invention, is represented in general at 10. The Image Recording and Tissue Mapping System 10 comprises a data acquisition and display module/controller 40 including microcomputer/storage/DVD ROM recording unit 41, display 3 and footpedal or other control 11. Foot pedal 11 is connected to microcomputer/storage/DVD ROM recording unit 41 via cable 15 and removably attachable connector 13. The Image Recording and Tissue Mapping System 10 also comprises position-tracking system 20, which includes, by way of example, position tracking module 22 and position sensor locator, such as a magnetic field transmitter 24. In addition, the Image Recording and Tissue Mapping System 10 also comprises a plurality of position sensors 32a, 32b and 32c affixed to the hand-held imaging probe 14. Although the hand-held imaging system 12 is shown as a subsystem separate from the scanning completeness auditing system 10, in some embodiments, the two systems are part of the same overall system. In some cases, the imaging device may be part of the scanning completeness auditing system.

Still referring to FIG. 31, hand-held imaging system 12 is connected to data acquisition and display module/controller 40 via data transmission cable 46 to enable each frame of imaging data (typically containing about 10 million pixels per frame) to be received by the microcomputer/storage/DVD ROM recording unit 41 the frequency of which is a function of the recording capabilities of the microcomputer/storage/DVD ROM recording unit 41 and the image data transmission capabilities, whether it is raw image data or video output of the processed image data, of the hand-held imaging system 12. Position information from the plurality of position sensors 32a, 32b, and 32c, is transmitted to the data acquisition and display module/controller 40 via the transmission cable 48. Cable 46 is removably attached to microcomputer/storage/DVD ROM recording unit 41 of data acquisition and display module/controller 40 with removably attachable connector 43 and is removably connected to diagnostic ultrasound system 12 with connector 47.

The position tracking module 22 is connected to data acquisition and display module/controller 40 via data transmission cable 48 wherein cable 48 is removably attached to microcomputer/storage/DVD ROM recording unit 41 of data acquisition and display module/control 40 with connector 45 and is removably connected to position tracking module with connector 49. Position sensor locator, such as a magnetic field transmitter 24 is connected to position tracking module 22 via cable 26 with removably attachable connector 25. Hand-held imaging probe assembly 30 includes, by way of example, position sensors 32a-32c, which are affixed to hand-held imaging probe 14 and communicate position data to position tracking module 22 via leads 34a-34c, respectively, and removably attachable connectors 36a-36c, respectively. Position sensor cables 34a-34c may be removably attached to ultrasound system cable 16 using cable support clamps 5a-5f at multiple locations as seen in FIG. 31.

Any suitable sensor may be used to provide location and position data. For example, magnetic sensors, optical markers (e.g. to be imaged by cameras), infrared markers, and ultraviolet sensors are examples of suitable options. Furthermore, a position sensor may or may not be a separate sensor added to the imaging device. In some cases, the sensor is a geometric or landmark feature of the imaging device, for example, the corners of the probe. In some embodiments, the optical, infrared, or ultraviolet cameras could capture an image of the probe and interpret the landmark feature as a unique position on the imaging device.

Although certain location and motion recognition methods have been described (e.g. FIG. 31), it can be appreciated that any location and motion recognition methods, software, devices, or systems can be used with the described embodiments. For example, sonar, radar, microwave, or any motion or location detection means and sensors may be employed.

Moreover, in some embodiments, sensors may not need to be added to the imaging device. Rather, location and motion detection systems can be used to track the position of the imaging device by using geometric or landmark features of the imaging device. For example, a location system may track the corners or edges of an ultrasound imaging probe while it is scanned across a target tissue.

Additionally, the sensors may also provide orientation data such as pitch, roll, and yaw. Such sensors may be position and/or orientation sensors that detect either position and/or orientation data. In some cases, a position sensor may only detect position. The system may then derive the undetected orientation information if needed.

In some embodiments, the Image Recording and Tissue Mapping System is configured to reconstruct an idealized tissue map as described above. The Image Recording and Tissue Mapping System may include computer software instructions or groups of instructions that cause a computer or processor to perform an action(s) and/or to make decisions. In some variations, the system may perform functions or actions such as by functionally equivalent circuits including an analog circuit, a digital signal processor circuit, an application specific integrated circuit (ASIC), or other logic device. In some embodiments, the Image Recording and Tissue Mapping System includes a processor or controller that performs the reconstruction functions or actions as described. The processor, controller, or computer may execute software or instructions for this purpose.

"Software", as used herein, includes but is not limited to one or more computer readable and/or executable instructions that cause a computer or other electronic device to perform functions, actions, and/or behave in a desired manner. The instructions may be embodied in various forms such as objects, routines, algorithms, modules or programs including separate applications or code from dynamically linked libraries. Software may also be implemented in various forms such as a stand-alone program, a function call, a servlet, an applet, instructions stored in a memory, part of an operating system or other type of executable instructions. It will be appreciated by one of ordinary skill in the art that the form of software may be dependent on, for example, requirements of a desired application, the environment it runs on, and/or the desires of a designer/programmer or the like. It will also be appreciated that computer-readable and/or executable instructions can be located in one logic and/or distributed between two or more communicating, co-operating, and/or parallel processing logics and thus can be loaded and/or executed in serial, parallel, massively parallel and other manners.

In some embodiments, the construction/reconstruction methods described may be performed by an imaging recording system that also performs additional other functions such as measuring coverage and resolution of images in a single and subsequent scan tracks. For example, the systems described in U.S. patent application Ser. No. 13/854,800 filed on Apr. 1, 2013; 61/753,832 filed Jan. 17, 2013; and 61/817,736 filed on Apr. 30, 2013, which are incorporated by reference in their entirety, may include processors, controllers, computers, or other components that are configured to reconstruct idealized images as described.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

The invention claimed is:

1. A tissue mapping system for constructing an idealized representation of a patient's scanned breast comprising:
   a recording system comprising a controller in communication with an imaging probe, the controller configured to electronically receive and record the scanned images from the imaging probe, to correlate recorded position of a region of interest to an idealized position of the region of interest on an idealized depiction of the anatomy and a position tracking system comprising at least one position and orientation sensor configured to provide data corresponding to the position and three-dimensional orientation of the imaging probe by generating position data for the scanned image from a plurality of position sensors providing data about positions of the imaging probe; electronically communicating the position data from the plurality of position sensors to a tissue map processor, wherein based on the position data the processor identifies a coronal plane for the patient, a first anterior-posterior projection through a tissue reference point to the coronal plane, and a second anterior-posterior projection through a probe reference point to the coronal plane; computing a relative angle between the first and second projections and medial-lateral vector through the tissue reference point; computing a distance between the first and second projections; constructing an idealized breast map based on the relative angle and distance computed; conforming the geometry of the recorded image to the idealized breast map; and depicting a recorded tissue feature in the idealized breast map by translating the recorded position of the tissue feature in the scanned image to a corresponding position in the idealized breast map.

2. The system of claim 1, wherein the controller is configured to determine a differential angle of a patient's coronal plane with reference to a plane of the floor.

3. The system of claim 1, wherein the controller is configured to append location identifier information to the scanned images from the imaging probe.

4. The system in claim 1, wherein the image recording and mapping system is configured to scale a medial-lateral location of a region of interest to fit the idealized depiction based on information from the position tracking system.

5. The system in claim 1, wherein the controller is configured to scale a superior-inferior location of a region of interest to fit the idealized depiction based on information from the position tracking system during the lateral and medial scans.

6. A method of constructing an idealized representation of a patient's scanned breast comprising:

recording a scanned image of the patient's breast obtained by an imaging probe;

generating position data for the scanned image from a plurality of position sensors providing data about positions of the imaging probe;

electronically communicating the position data from the plurality of position sensors to a tissue map processor, wherein based on the position data the processor identifies a coronal plane for the patient, a first anterior-posterior projection through a tissue reference point to the coronal plane, and a second anterior-posterior projection through a probe reference point to the coronal plane;

computing a relative angle between the first and second projections and medial-lateral vector through the tissue reference point;

computing a distance between the first and second projections;

constructing an idealized breast map based on the relative angle and distance computed;

conforming the geometry of the recorded image to the idealized breast map; and depicting a recorded tissue feature in the idealized breast map by translating the recorded position of the tissue feature in the scanned image to a corresponding position in the idealized breast map.

7. The method of claim 6, wherein the processor is configured to identify a relative coronal plane of the breast, a nipple-to-middle-of-chest-wall vector, medial and lateral boundaries, superior and inferior boundaries, a sagittal plane for the patient, a coronal plane for the patient, and a medial-lateral alignment for the patient.

8. The method of claim 6, further comprising scaling the scanned image to the size and shape of the idealized map.

9. The method of claim 6, wherein the processor is configured to apply trigonometric reconstruction to generate the idealized map.

10. The method of claim 6, wherein the processor is configured to apply geometric reconstruction to generate the idealized map.

* * * * *